United States Patent [19]

Lee

[11] Patent Number: 5,013,850

[45] Date of Patent: May 7, 1991

[54] 4-ETHYL AND 4-ETHENYL-5-HYDROXY-2(5H)-FURANONES SUBSTITUTED ON ALPHA CARBON OF THE ETHYL OR ETHENYL SIDE CHAIN WITH A LONG CHAIN ALKYL GROUP AND ON THE BETA CARBON WITH A POLAR GROUP, AS ANTI-INFLAMMATORY AGENTS

[75] Inventor: Gary C. M. Lee, Laguna Hills, Calif.

[73] Assignee: Allergan, Inc., Irvine, Calif.

[21] Appl. No.: 502,208

[22] Filed: Mar. 30, 1990

[51] Int. Cl.$^5$ ................... C07F 9/28; C07D 305/12
[52] U.S. Cl. .................... 549/222; 549/318; 549/321
[58] Field of Search .................... 549/222, 318, 321

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,455 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |

FOREIGN PATENT DOCUMENTS

| | | |
|---|---|---|
| 133376 | 2/1985 | European Pat. Off. |
| 209274 | 1/1987 | European Pat. Off. |
| 295056 | 6/1987 | European Pat. Off. |

OTHER PUBLICATIONS

Bonjouklian, et al., Chemical Abstracts, vol. 106, 156260c, p. 670 (1987).

Reynolds, et al., J. Am. Chem. Soc., 110, pp. 5172-5177 (1988).

Tocanne et al., Chemical Abstracts 69 76581k, p. 7146 (1968).

Deems, et al., Biochimica et Biophysica Acta, 917, pp. 258-268 (1987).

Scheuer et al., Journal of the American Chemical Society 100:1, p. 307 (Jan. 4, 1978).

Graziano, et al., Chemical Abstracts 107, (1987), 236559t.

Negishi et al., J. Org. Chem. 45, pp. 5223-5225, (1980).

Primary Examiner—Cecilia Shen
Attorney, Agent, or Firm—Gabor L. Szekeres; Martin A. Voet; Robert J. Baran

[57] ABSTRACT

Compounds of Formula 1, and of Formula 2,

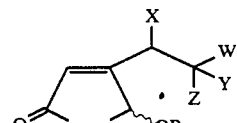

Formula 1

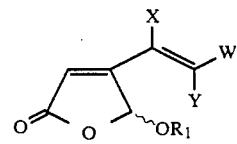

Formula 2 in which $R_1$ is H or alkyl of 1 to 20 carbon, CO—$R_1^*$ CO—O—$R_1^*$ CO—NH—$R_1^*$ or PO(O$R_1^*$)$_2$ or PO(O$R_1^*$)$R_1^*$ where $R_1^*$ independently is alkyl of 1 to 20 carbons, phenyl, or substituted phenyl; X is long chain alkyl having at least 5 carbon atoms, long chain alkyl of at least 5 carbons substituted with an aryl group, or long chain alkyl of at least 5 carbons substituted with a substituted aryl group; Y is COOH, COOR$_2$, CONH$_2$, CONHR$_2$, CON(R$_2$)$_2$, CHO, COR$_2$; COCF$_3$, COCHF$_2$, CH=NR$_2$, CR$_2$=N—R$_2$, CH=N—NHR$_2$, CH=N—N(R$_2$)$_2$, CH=NOH, CR$_2$=N—OH, CH=NOR$_2$, CR$_2$=NOR$_2$, CH$_2$OH, CHR$_2$OH, C(R$_2$)$_2$OH, CH$_2$OR$_2^*$ CHR$_2$OR$_2^*$ C(R$_2$)$_2$OR$_2^*$ SO$_2$R$_2$, PO(OR$_3$)$_2$, and PS(OR$_3$)$_2$, where R$_2$ independently is alkyl, phenyl, or substituted phenyl, R$_2^*$ is alkyl, phenyl, substituted phenyl, alkanoyl, or aroyl, and R$_3$ is H, alkyl, phenyl or substituted phenyl; W is H, alkyl, phenyl, COOH, COOR$_4$, CONHR$_4$, CON(R$_4$)$_2$, and Z is H or alkyl, are disclosed. The compounds possess anti-inflammatory activity.

53 Claims, No Drawings

4-ETHYL AND 4-ETHENYL-5-HYDROXY-2(5H)-FURANONES SUBSTITUTED ON ALPHA CARBON OF THE ETHYL OR ETHENYL SIDE CHAIN WITH A LONG CHAIN ALKYL GROUP AND ON THE BETA CARBON WITH A POLAR GROUP, AS ANTI-INFLAMMATORY AGENTS

BACKGROUND OF THE INVENTION

1. Field of the Invention

The present invention is directed to novel 4-ethyl and 4-ethenyl-5-hydroxy-2(5H)-furanones substituted on the alpha carbon of the ethyl or ethenyl side chain with a long chain alkyl group and on the beta carbon with a polar group, which compounds are active as anti-inflammatory agents. The present invention is also directed to pharmaceutical compositions which comprise one or more of the novel compounds of the invention, to the methods of using these pharmaceutical compositions, and to the chemical processes of making the novel compounds.

2. Brief Description of the Prior Art Manoalide is a compound isolated from a marine sponge [E. D. de Silva et al., *Tetrahedron Letters* 21:1611–1614 (1980)] which has anti-inflammatory, immunosuppressive and analgesic properties. Manoalide (Compound 1) the structure of which is shown below, includes a 5-hydroxy-2(5H)-furanone moiety, attached in the 4-position of the furanone ring to the rest of the molecule. Certain analogs of manolide, such as seco-manoalide (Compound 2) and dehydro-seco-manoalide (Compound 3) also have anti-inflammatory inflammatory activity. For further description of the biological activity of manoalide and some of its derivatives reference is made to U.S. Pat. No. 4,447,445 and to European Patent Application No. 0133376 (published on Feb. 20, 1985).

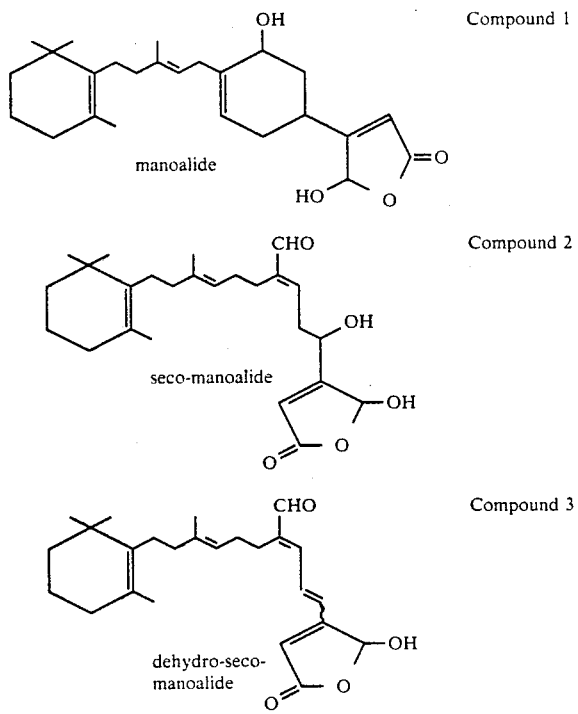

manoalide — Compound 1 seco-manoalide — Compound 2 dehydro-seco-manoalide — Compound 3

Synthetic analogs of manoalide, particularly analogs having various substituents on the furanone moiety of manoalide, are described in several applications for United States Letters Patent by the same inventor as in the present application, the following of which have been allowed and are expected to issue as United States Letters Patent:

Ser. No. 259,225 filed on Oct. 18, 1988;
Ser. No. 281,126 filed on Dec. 7, 1988.

Published European Patent Application No. 0 295 056 discloses 4-substituted 5-hydroxy-2(5H)-furanones having anti-inflammatory, immunosuppressive and anti-proliferative activity where the substituents in the 4 position are a variety 1-hydroxyalkyl, 1-acyloxy-alkyl and 1-carbamoyloxy-alkyl groups.

SUMMARY OF THE INVENTION

The present invention covers compounds of Formula 1, and of Formula 2,

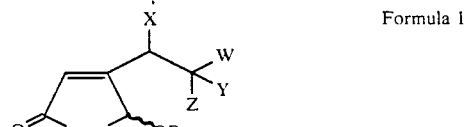

Formula 1

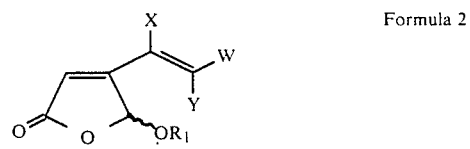

Formula 2 in which $R_1$ is H or alkyl of 1 to 20 carbons, $CO-R_1^*$ $CO-O-R_1^*$ $CO-NH-R_1^*$ or $PO(OR_1^*)_2$ or $PO(OR_1^*)R_1^*$ where $R_1^*$ independently is alkyl of 1 to 20 carbons, phenyl, or substituted phenyl;

X is long chain alkyl having at least 5 carbon atoms, long chain alkyl of at least 5 carbons substituted with an aryl group, or long chain alkyl of at least 5 carbons substituted with a substituted aryl group;

Y is $COOH$, $COOR_2$, $CONH_2$, $CONHR_2$, $CON(R_2)_2$, $CHO$, $COR_2$; $COCF_3$, $COCHF_2$, $CH=NR_2$, $CR_2=N-R_2$, $CH=N-NHR_2$, $CH=N-N(R_2)_2$, $CH=NOH$, $CR_2=N-OH$, $CH=NOR_2$, $CR_2=NOR_2$, $CH_2OH$, $CHR_{20}OH$, $C(R_2)_2OH$, $CH_2OR_2^*$ $CHR_2OR_2^*$ $C(R_2)_2OR_2^*$ $SO_2R_2$, $PO(OR_3)_2$, and $PS(OR_3)_2$, where $R_2$ independently is alkyl, phenyl, or substituted phenyl, $R_2^*$ is alkyl, phenyl, substituted phenyl, alkanoyl, or aroyl, and $R_3$ is H, alkyl, phenyl or substituted phenyl; W is H, alkyl, phenyl, $COOH$, $COOR_4$, $CONHR_4$, $CON(R_4)_2$, and Z is H or alkyl.

The present invention also covers salts of the above-defined compounds, formed with pharmaceutically acceptable acids or bases, as applicable.

In a second aspect the present invention relates to pharmaceutical formulations comprising one or more compounds of Formula 1 or one or more compounds of Formula 2 (or pharmaceutically acceptable salts therof) in admixture with a pharmaceutically excipient, for the purpose of treating certain conditions, syndromes or diseases in mammals, including humans. The compounds of the invention have anti-inflammatory, immunosuppressant and anti-proliferative activity. Therefore, the compounds are useful for treating in mammals (including humans) inflammation, rheumatoid arthritis, osteoarthritis, rheumatic carditis, ocular and dermal inflammatory diseases, autoimmune diseases such as allergic diseases, bronchial asthma and myasthenia gravis, and for suppressing unwanted immune responses and retarding proliferation of cell.

In still another aspect, the present invention relates to the processes of making the compounds of Formula 1, and the compounds of Formula 2. In general terms, these processes comprise the steps of reacting a 2-trialkylsilyl-4-furaldehyde (Formula 3) with a Grignard reagent (or the like) which introduces the "long chain" alkyl group X as substituent on the alpha carbon of the side chain of the desired compounds of Formula 1 and Formula 2 (aldehyde carbon in Formula 3) and simultaneously forms a secondary alcohol on the alpha carbon. The secondary alcohol is then oxidized to the corresponding ketone (Formula 4), and the ketone alkylated with a reagent of Formula 5 which carries the Y subtituent, or a suitable precursor of the Y substituent (designated as Y' in Formula 5, L is a leaving group or represents Mg-Br or the like; the reagent of Formula 5 is a Reformatskii or Grignard reagent or the like). The intermediate tertiary alcohol obtained as a result of reaction of the ketone of Formula 4 with the reagent of Formula 5 is dehydrated to provide a 4-ethenyl-2-trialkylsilyl furan derivative shown in Formula 6. The 4-ethenyl-2-trialkylsilyl furan derivative of Formula 6 is subjected to treatment with singlet oxygen to provide the compounds of Formula 2 where $R_1$ is hydrogen. Alternatively, the olefinic double bond in the ethenyl side chain of the compounds of Formula 6 is saturated to provide the 2-trialkylsilyl furan derivatives shown in Formula 7. Treatment of compounds of Formula 7 with singlet oxygen provides the compounds of Formula 1 where $R_1$ is hydrogen. The just described reaction steps are schematically shown in Reaction Scheme 1.

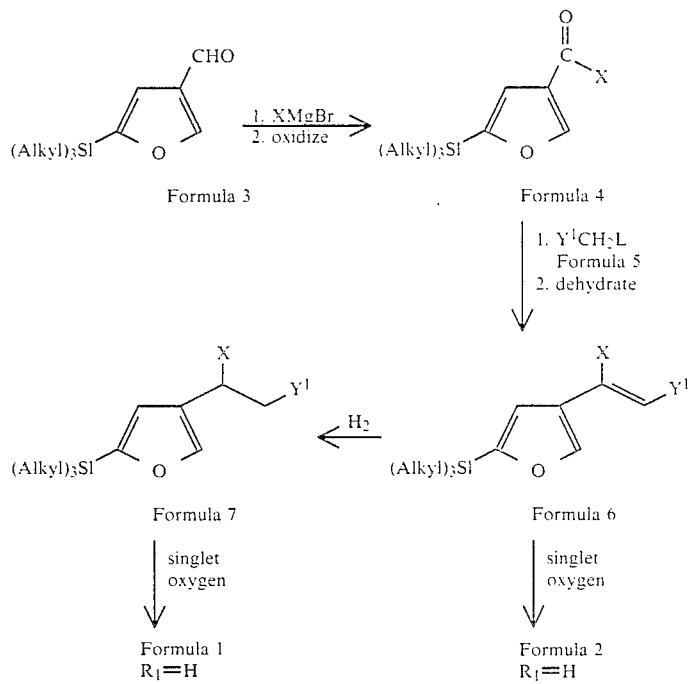

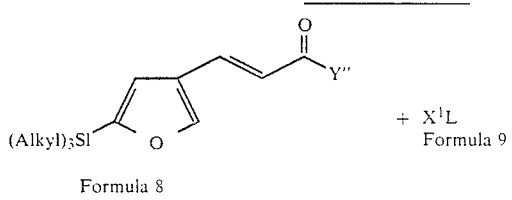

Reaction Scheme 2

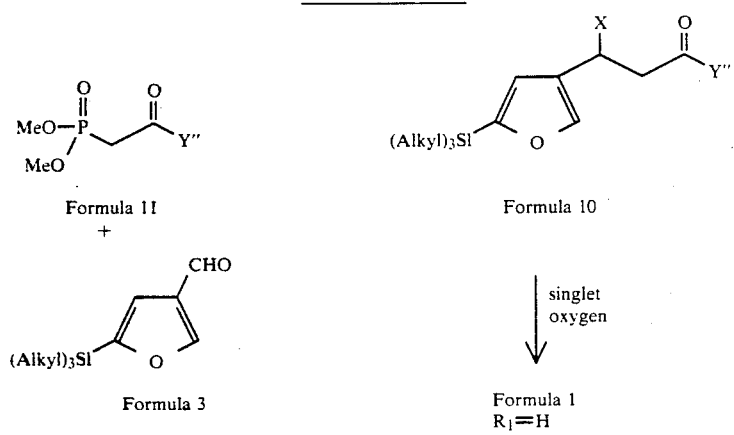

Formula 11

+

Formula 10

Formula 3 singlet oxygen

↓

Formula 1
$R_1 = H$

In another general synthetic route to the compounds of the invention (Reaction Scheme 2) a compound of Formula 8 is reacted in a 1,4-Michael addition (or like) reaction with a reagent of Formula 9 to introduce the X substituent on the alpha carbon of the side chain. In Formula 8, CO and Y" jointly symbolize a carbonyl function included in the Y group (as Y is defined in connection with Formula 1), or CO—Y" symbolizes such derivatives or precursors of the Y group which can be readily converted into the Y group by chemical reactions within the skill of the ordinary artisan in the field of synthetic organic chemistry. X'—L symbolizes a reagent which is capable of undergoing a 1,4-(Michael) addition (or like) reaction on the alpha, beta-unsaturated carbonyl system of the compounds of Formula 8, X' either represents X (as X is defined in connection with Formula 1) or X' represents such derivatives or precursors of the X group which can be readily converted into the X group by chemical reactions within the skill of the ordinary artisan in the field of synthetic organic chemistry.

The compounds of Formula 8 can be obtained, in several ways, for example by reaction of a Wittig-Horner type reagent of Formula 11 (or a Wittig reagent) with a 2-trialkylsilyl-4-furaldehyde (Formula 3). The 2-trialkylsilylfuran derivatives of Formula 10 are treated with singlet oxygen to yield the compounds of Formula 1 where $R_1$ is H. The $R_1$ substituent (as defined in connection with Formula 1) can be introduced into the 5-hydroxy-2(5H)-furanones of the invention by reaction (such as acylation) well known in the field.

Reaction Scheme 3

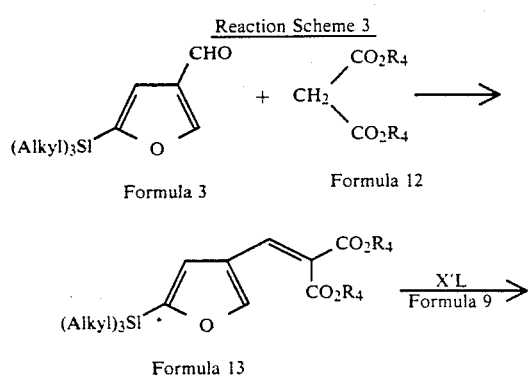

Formula 3 + Formula 12

→

Formula 13

-continued
Reaction Scheme 3

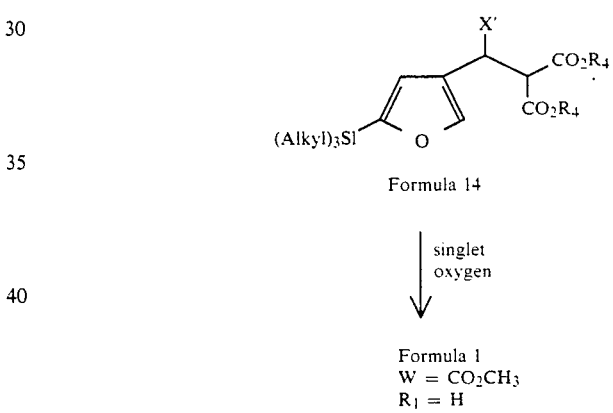

Formula 14 singlet oxygen

↓

Formula 1
W = $CO_2CH_3$
$R_1 = H$

As still another process for making the compounds of the invention, an alpha, beta-unsaturated carbonyl system (similar to the one shown in Formula 8) can be introduced into the furan molecule by reacting a 2-trialkylsilyl-4-furaldehyde (Formula 3) with a malonic ester of Formula 12, as is shown in Reaction Scheme 3, to yield the compounds of Formula 13. In Formula 12 $R_2$ and $R_4$ are defined as in connection with Formula 1 The compounds of Formula 13 are then reacted with the 1,4-(Michael) addition reagent of Formula 9 to provide the 2-trialkylsilylfuran derivatives of Formula 14 where the alpha carbon of the side chain bears the desired X substituent, or such an X' substituent which can be readily converted into the X group by reactions well known in the art. The compounds of Formula 14 are reacted with singlet oxygen to provide the compounds of Formula 1 where W is $COOR_4$ and $R_1$ is hydrogen.

Compounds of the invention where the Y substituent bears an alcohol group (for example Y is $C(R_2)_2OH$, $R_2$ is defined as in Formula 1) can be obtained by a reacting the intermediate of Formula 10 with a Grignard reagent of the Formula $R_2$-Mg-Br, followed by treatment with singlet oxygen.

Reaction Scheme 4

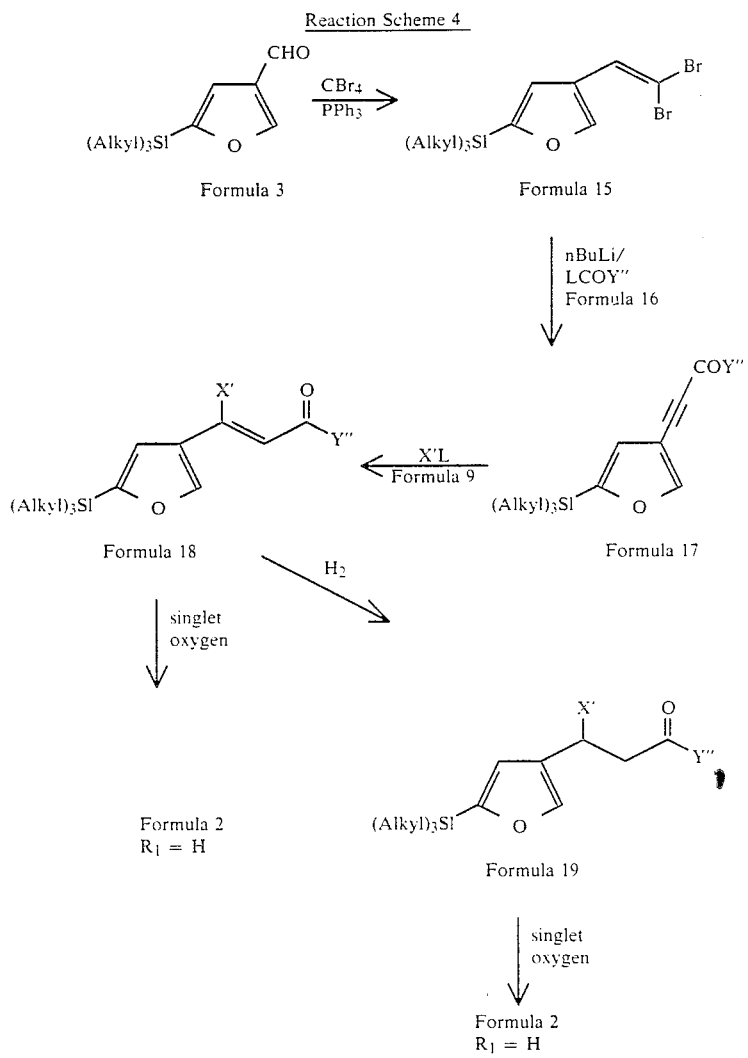

As a still further general route to the compounds of the invention (Reaction Scheme 4) the 2-trialkylsilyl-4-furaldehyde (Formula 3) is reacted with a Wittig reagent derived from carbontetrabromide (CBr$_4$) and triphenylphosphine (P(C$_6$H$_5$)$_3$). The resulting 2-trialkylsilyl-4-(2,2-dibromo)ethenylfurans of Formula 15 are reacted with n butyl lithium and a reagent L—CO—Y" (Formula 16) which introduces the Y substituent into the molecule. Co—Y" is defined as above in connection with Reaction Scheme 2. In the just noted reaction of the 2,2-dibromo ethene compounds of Formula 15 the strong base (n-butyl lithium) first causes formation of a triple bond by elimination, followed by halogen lithium exchange to provide a strongly nucleopholic lithium acetylide which reacts with the reagent of Formula 16. The L function in L—CO—Y" (Formula 16) symbolizes a leaving group, such as an O-alkyl group, which is capable of reacting with the intermediate lithium acetylide to yield the 4-ethynyl substituted 2-trialkylsilyfuran derivatives of Formula 17. The compounds of Formula 17 are then subjected to a 1,4-(Michael) addition reaction (or the like) with a reagent X'—L (defined as above in connection with Reaction Scheme 2). This last reaction (Michael addition) results in an ethenyl derivative of Formula 18, which is reacted with singlet oxygen to provide compounds of Formula 2 where R$_1$ is hydrogen. Alternatively, the ethenyl derivatives (Formula 18) are hydrogenated to yield the 2-trialkylsilylfurans of Formula 19, which, after treatment with singlet oxygen, provide the compounds of Formula 1 where R$_1$ is hydrogen.

Reaction Scheme 5

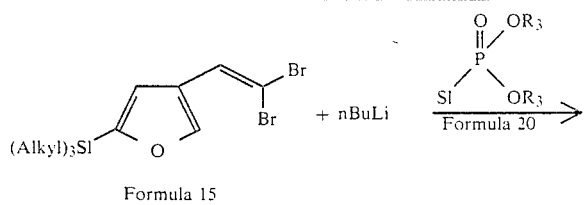

Reaction Scheme 5

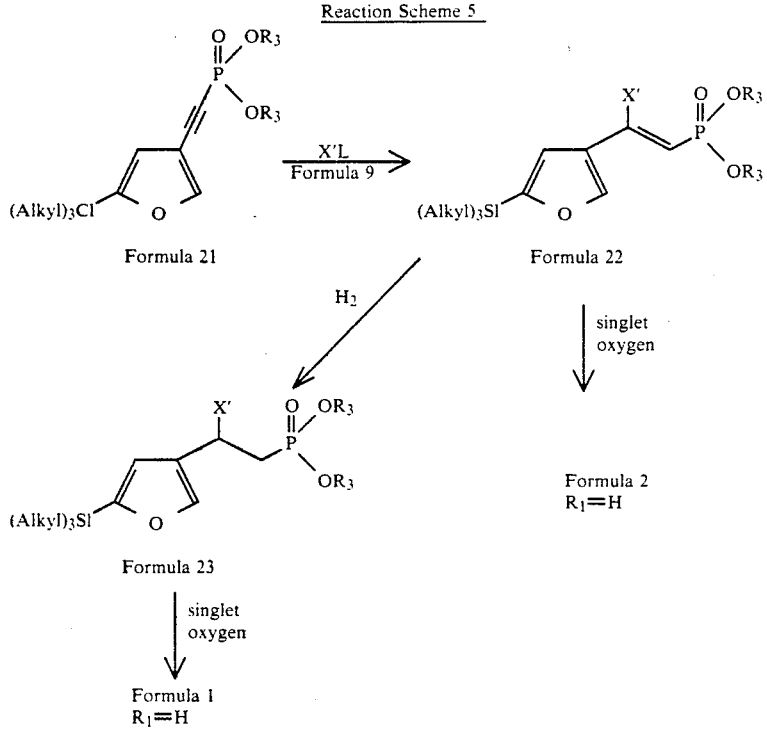

Compounds of the invention where Y is $SO_2R_2$, $PO(OR_3)_2$, and $PS(OR_3)_2$, ($R_2$ and $R_3$ are defined as in connection with Formula 1) are, generally speaking, prepared by reacting the intermediates of Formula 15 with a dialkyl chlorophosphate (Formula 20, $R_3$ is defined as above but in this reaction is not hydrogen) in the presence of strong base, such as n-butyl lithium. (Reaction Scheme 5). The resulting dialkylphosphonyl acetylene derivative (Formula 21) is thereafter subjected to reaction steps similar to those described in connection with Reaction Scheme 4, namely the X substituent is introduced to the alpha carbon by a 1,4-(Michael) addition using the reagent of Formula 9. The resulting intermediate 2-trialkylsilyl-4-(dialkylphosphonyl)ethenyl-furan derivatives (Formula 22) are subjected to singlet oxygen to provide the compounds of Formula 2 where $R_1$ is hydrogen. Alternatively, the intermediate 2-trialkylsilyl-4(dialkylphosphenyl)ethenylfuran derivatives (Formula 22) are subjected to singlet oxygen to provide the compounds of Formula 2 where $R_1$ is hydrogen. Alternatively, the intermediate 2-trialkylsilyl-4-(dialkylphosphenyl)ethenylfuran derivatives (Formula 22) are hydrogenated to yield the corresponding 2-trialkylsilyl-4-(dialkylphosphonyl)ethylfuran derivatives (Formula 23) which, after treatment with singlet oxygen yield the compounds of Formula 1, where $R_1$ is H.

Compounds of Formula 1 and of Formula 2 where Y is $SO_2R_2$, or $PS(OR_3)_2$, ($R_2$ and $R_3$ are defined as in connection with Formula 1) are prepared in reaction sequences analoguous to the sequence shown in Reaction Scheme 5, except that, instead of a chlorophosphate (Formula 20), a chlorothiophosphate or a chlorosulphonate is used.

In another general aspect, the processes leading to the compounds of the invention involve performance of routine chemical reactions (such as esterification, saponification of esters, oxidation of alcohols to ketones or aldehydes, formation of oximes and hydrazones from aldehydes or ketones, and the like) which are well known to the practicing synthetic organic chemist.

When it is desired to substitute (acylate, alkylate or the like) the 5-hydroxy function of the compounds of Formula 1 and 2, an $R_1$ group (as defined in connection with these formulas) can be introduced into the 5-hydroxy-2(5H)-furanone compounds by conventional means.

GENERAL EMBODIMENTS

Definitions

The terms "ester", "amine", "amide", "ether" and all other terms and terminology used here, (unless specifically defined in the present description) refer to and cover any compounds falling within the respective term as that term is classically used in organic chemistry.

Unless specifically noted otherwise, preferred esters are derived from the saturated aliphatic alcohols or acids of ten or fewer carbon atoms or from the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

The term "alkyl" as used in the present description and claims includes straight chain alkyl groups, branched chain alkyl groups, cycloalkyl groups, alkyl substituted cycloalkyl groups, and cycloalkyl substituted alkyl groups. Unless the number of carbons is otherwise specified, "lower alkyl" means the former broad definition of "alkyl" groups but with the restriction that the group has 1 to 6 carbon atoms.

The term "long chain alkyl" also means the former broad definition of "alkyl" groups but with the restriction that the group has no less than 4 carbon atoms, and no more than approximately 25 carbon atoms.

Unless specifically noted otherwise, preferred amides are the mono- and di-substituted amides derived from the saturated aliphatic radicals of ten or fewer carbon atoms, or the cyclic or saturated aliphatic-cyclic radicals of 5 to 10 carbon atoms.

Some of the compounds of the invention (Formula 1) contain a chiral center at the alpha carbon in the side chain on the 4-position of the furan ring. Other compounds of the invention may contain one or more additional chiral centers. Accordingly, the compounds of the invention may be prepared as mixtures of enantiomeric compounds (where the enatiomers may or may not be present in equal amounts) or as optically pure enantiomers. When there is more than one chiral center, the compounds of the invention may also be prepared as mixtures of diastereomers, or as pure diastereomers, and each diastereomer itself may be a mixture of enantiomers in 1:1, or other, ratios. Alternatively, each diastereomeric compound may be sterically and optically pure. However, all of the above-noted forms, including optically pure enantiomers and mixtures thereof, as well as all diastereomers, are within scope of the present invention.

Some of the compounds of the invention (Formula 2) may have cis and trans stereoisomers. The scope of the invention includes both pure stereoisomers as well as mixtures thereof.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkylamines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of the present invention are, with reference to Formula 1 and Formula 2 and with respect to the 5-position of the furanone moiety, those where the substituent is hydroxy or acetoxy ($R_1$ is H or $CH_3CO$).

With respect to the Z substituent on the beta carbon in the side chain (in the 4-position) of the furanone moiety (Formula 1), the preferred compounds of the invention are those where Z is hydrogen. These compounds are, generally speaking, made by the processes of Reaction Schemes 1 through 5.

With respect to the W substituent on the beta carbon of the side chain in the 4-position of the furanone molecule, the preferred compounds of the invention are those where W is hydrogen, or is $COOR_4$ ($R_4$ defined as in Formula 1), preferably $R_4$ is methyl. The compounds where W is hydrogen are, generally synthesized by the processes of Reaction Schemes 1, 2, 4 and 5, whereas the compounds where W is $COOR_4$ are, generally speaking, synthesized by the processes shown in Reaction Scheme 3.

With respect to the X substituent on the alpha carbon of the side chain in the 4-position of the furanone molecule, the preferred compounds of the invention are those where X is long chain alkyl of more than 8 carbons, or X is 5-(phenyl)pentyl, or a derivative substituted in the phenyl ring. Particularly preferred in this regard are compounds where X is $CH_3(CH_2)_{11}$, and compounds where X is 5-(2,4,5-trifluorophenyl)pentyl. Generally speaking, these compounds are synthesized by the reaction sequences outlined in Reaction Schemes 1 through 5, the X group being introduced either through a Grignard reagent (Reaction Scheme 1) or as a reagent X'—L capable of undergoing a 1,4-(Michael) addition (Reaction Schemes 2 through 5). The Michael addition reagent preferably is a "cuprate" derived from an alkylhalide, preferably alkyliodide, X'—I (or aralkyl halide, preferably iodide) by treatment with zinc, and copper (I) cyanide. The resulting complex of the structure X—Cu(CN)ZnI is the preferred 1,4-(Michael) addition reagent in the processes of the present invention.

With respect to the Y substituent on the beta carbon of the side chain in the 4-position of the furanone molecule, the preferred compounds of the invention are those where Y is COOH, $COOR_2$, $CONH_2$ with $R_2$ in these ester preferably being lower alkyl, most preferably methyl or ethyl. Compounds are also preferred where Y is $COR_2$, $COCF_3$, $COCF_2H$, with $R_2$ preferably being methyl in these ketone compounds. Still further, compounds are preferred where Y is CH=NOH, or $CH=NOR_2$ (aldoximes), $CR_2=NOH$, $CR_2=NOR_2$ (ketoximes) and $CH=N-NHR_2$ (hydrazones) with R2 preferably being methyl in these oxime or hydrazone compounds. Other preferred compounds are where Y is $C(R_2)_2OH$ (tertiary alcohols, with $R_2$ preferably being methyl) and where Y is $PO(OR_3)_2$, $PS(OR_3)_2$, $SO_2R_2$ (phosphonyl, thiophosphonyl and sulphonyl compounds). The sulphonyl compounds are particularly preferred where $R_2$ is methyl, and phosphonyl compounds are particularly preferred where $R_3$ is ethyl.

The Y substituent is introduced into the molecule in accordance with the Reaction Schemes 1 through 5. More particularly, with reference to Reaction Scheme 1 the Y'—$CH_2$—L reagent (Formula 5) is preferably a Reformatskii reagent, such as the one derived from ethyl bromoacetate with zinc. Alternatively, the Y group is introduced into the molecule by reacting the 2-trialkylsilyl-4-furaldehyde (Formula 3) with a Wittig or Wittig Horner reagent (Reaction Scheme 2 and 4) or with a malonic acid ester. In this regard 2-trimethylsilyl-4-furaldehyde (Compound 4), 2-triethylsilyl-4-furaldehyde (Compound 5) and 2-tert butyldimethylsilyl)-4-furaldehyde (Compound 6) are preferred starting materials. These starting materials (Compounds 4, 5 and 6) can be made in accordance with several procedures known in the chemical literature. The preferred method for the synthesis of these compounds, however, is described in the application for United States Letters Patent Ser. No. 259,225, filed on Oct. 18, 1988, now allowed, and assigned to the same assignee as the present application. The processes for the syntheses of these important starting materials are also described here in detail in the ensuing section of Specific Examples. Preferred Wittig and Wittig Horner reagents for the introduction of the Y group are derived for example from triphenylphosphine, particularly from triphenylphosphine and tetrabromomethane. The Wittig, Wittig Horner and malonic acid ester (preferably malonic acid dimethyl ester) reagents used in the reactions are either commercially available, or can be prepared in accordance with ordinary skill in the art.

In each of the synthetic routes utilized for the preparation of the compounds of the present invention, an important reaction is the treatment of a 2-trialkylsilyl-4-substituted furan (Formulas 6, 7, 10, 14, 18, 19 22 and 23) with singlet oxygen to provide the 4-substituted 5-hydroxy-2(5H)-furanones of the present invention. As a result of this reaction step, the trialkylsilyl group is "removed" from the furan molecule, an oxo funtion is introduced into the 2-position and a hydroxy function is introduced into the 5-position. This reaction is indicated on each of the Reaction Schemes 1-5 to yield compounds of Formula 1 or of Formula 2 where $R_1$ is hydrogen. In the event, substitution on the 5-hydroxy group is desired, this can be accomplished with conventional means.

Referring back again to the reaction of the 2-trialkylsilyl intermediates of Formula 6, 7, 10, 14, 18, 19 22 and 23 with singlet oxygen, the conditions of these reactions are described below in connection with several specific examples. In general terms, the reaction is preferably conducted in a mixture of water and acetone or in a mixture of water and tetrahydrofuran in the presence of an initiator, preferably Rose Bengal dye (preferably polymer bounded), which is added to the reaction mixture. The reaction mixture and vessel is flushed with oxygen and the reaction is conducted at low temperature, preferably between approximately $-78°$ C. and $0°$ C., under a constant positive pressure of oxygen for a number of hours, typically 1 to 6 hours. The mixture is typically irradiated with a 150 Watt flood lamp. Workup of the reaction mixture after irradiation usually includes concentration by evaporation of the solvent, followed by chromatography on silica gel, in columns or on preparative silica plates.

In the event the X' or Y' groups of intermediates require chemical modification (such as removal of a protecting group, or other modification) to provide the desired X and Y groups respectively, such synthetic modifications are typically and preferably accomplished before reaction of the respective intermediate with singlet oxygen.

The most preferred compounds of the invention are those listed just below with reference to Formula 24 or Formula 25:

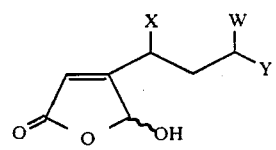

Formula 24

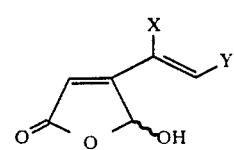

Formula 25

Formula 24, Compound 7: W=H, X=CH$_3$—(CH$_2$)$_{11}$ and Y=CO$_2$CH$_2$CH$_3$;

Formula 24, Compound 8: W=H, X=CH$_3$—(CH$_2$)$_{11}$ and Y=COCH$_3$;
Formula 24, Compound 9: W=H, X=CH$_3$—(CH$_2$)$_{11}$ and Y=COCF$_3$;
Formula 24, Compound 10: W=H, X=CH$_3$—(CH$_2$)$_{11}$ and Y=C(CH$_3$)$_2$OH;
Formula 24, Compound 11: W=CO$_2$CH$_3$, X=CH$_3$—(CH$_2$)$_{11}$ and Y=CO$_2$CH$_3$;
Formula 24, Compound 12: W=H, X=CH$_3$—(CH$_2$)$_{11}$ and Y=COOH;
Formula 24, Compound 13: W=H, X=CH$_3$—(CH$_2$)$_{11}$ and Y=PO(OCH$_2$CH$_3$)$_2$;
Formula 24, Compound 14: W=H, X=5-(2,4,5-trifluorophenyl)pentyl and Y=COCF$_3$;
Formula 24, Compound 15: W=H, X=CH$_3$—(CH$_2$)$_{11}$ and Y=CH=NOCH$_3$;
Formula 24, Compound 16: W=H, X=CH$_3$—(CH$_2$)$_{11}$ and Y=CONH$_2$;
Formula 24, Compound 17: W=H, X=CH$_3$—(CH$_2$)$_{11}$ and Y=CH=NOH;
Formula 24, Compound 18: W=H, X=CH$_3$—(CH$_2$)$_{11}$ and Y=CH=NNHCH$_3$;
Formula 24, Compound 19: W=H, X=CH$_3$—(CH$_2$)$_{11}$ and Y=COCF$_2$H;
Formula 24, Compound 20: W=H, X=CH$_3$—(CH$_2$)$_{11}$ and Y=PS(OCH$_2$CH$_3$)$_2$;
Formula 24, Compound 21: W=H, X=CH$_3$—(CH$_2$)$_{11}$ and Y=SO$_2$CH$_3$;
Formula 24, Compound 22: W=H, X=CH$_3$—(CH$_2$)$_{11}$ and Y=CCH$_3$=NOH;
Formula 25, Compound 23: X=CH$_3$—(CH$_2$)$_{11}$ and Y=COCF$_3$, and
Formula 25, Compound 24: X=CH$_3$—(CH$_2$)$_{11}$ and Y=PO(OCH$_2$CH$_3$)$_2$;

The compounds of the present invention are useful in pharmaceutical compositions to produce anti-inflammatory, immunosuppressant and anti-proliferative activity. The diseases, syndromes or conditions of mammals (including humans) which can be treated with pharmaceutical compositions containing one or more compounds of the invention (or salts thereof) include: inflammation, rheumatoid arthritis, osteoarthritis, rheumatic carditis, ocular and dermal inflammatory diseases, autoimmune diseases such as allergic diseases, bronchial asthma and myasthenia gravis, unwanted immune responses and unwanted proliferation of cells, psoriasis, acne, atopic diseases and allergic conjunctivitis.

The activity of the compounds of this invention is demonstrated by inhibition of the enzyme phospholipase A$_2$ in vitro and by reduction of inflammation in the mouse ear anti-inflammatory assay in vivo.

Activity of compounds of this invention may also be demonstrated by inhibition of phosphoinositide-specific phospholipase C. This activity has been reported for manoalide and may indicate anti-inflammatory utility. Bennett et al, *Molecular Pharmacology* 32:587-593 (1987).

Activity of the compounds may also be demonstrated by inhibition of ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells, GH$_3$ cells, etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or Cl$^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppressive properties.

In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula I and of Formula 2, and pharmaceutical carriers suitable for the route of administration. Standard methods for formulating pharmaceutical compositions of this type may be found in *Remington's Pharmaceutical Sciences,* Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05-5% of the active ingredient.

A typical cream formulation may contain the following:

| Ingredient | Parts by Weight |
| --- | --- |
| Water/glycol mixture (15% or more glycol) | 50-99 |
| Fatty alcohol | 1-20 |
| Non-ionic surfactant | 0-10 |
| Mineral oil | 0-10 |
| Typical pharmaceutical adjuvants | 0-5 |
| Active ingredient | 0.05-5 |

A typical ointment formulation may contain the following:

| Ingredients | Parts by Weight |
| --- | --- |
| White petrolatum | 40-94 |
| Mineral oil | 5-20 |
| Glycol solvent | 1-15 |
| Surfactant | 0-10 |
| Stabilizer | 0-10 |
| Active ingredient | 0.05-5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40-99 |
| Magnesium stearate | 1-2 |
| Cornstarch | 10-20 |
| Active ingredient | 0.001-20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The assay procedures by which useful biological activity of the compounds of the invention can be demonstrated, are described below.

Calcium Channel (mobilization) Inhibition Assay

Polymorphonuclear leukocytes (PMNa), gastric glands, GH$_3$ cells, A431 cells, spleen cells, human keratinocytes corneal cells, etc. were loaded with the Ca$^{2+}$ sensitive fluorescent dye, Fura-2. The appropriate cell type was chosen and the potency and efficacy of the anti-inflammatory furanones on calcium mobilization, calcium channel inhibition was quantitated. The methods used for A431 cells listed below are representative of those used for other cells.

A431 cells were detached using a 5-10 min trypsin-EDTA treatment whereas GH$_3$ cells were treated 2 to 5 min with a 1% pancreatin solution. Cells were immediately washed twice in a 20 mM HEPES buffer (pH 7.4) containing 120 mM NaCl, 6 mM KCl, 1 mM MgSO$_4$, 1 mg/ml glucose and 1 mg/ml pyruvate and 1.4 mM calcium (medium A). Approximately $5 \times 10^6$ cells were suspended in medium A and incubated with 4 uM fura-2-AM for 15 min at 37° C.

After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340 nm and emission wavelength set at 500 nm. The cell suspension was continually stirred, maintained at 37° C. and equilibrated for approximately 5 min before addition of various agents. [Ca$^{2+}$i was calculated using the following formula:

$$[Ca^{2+}]_i = 220 \times \frac{F - F\text{min}}{F\text{max} - F}$$

All fluorescence values were measured relative to a EGTA-quenched signal determined as follows: F was the relative fluorescence measurement of the sample. F$_{max}$ was determined by lysing the cells with digitonin (100 ug/ml) in DMSO. After F$_{max}$ was determined the pH was adjusted to 8, with NaOH and Ca$^{2+}$ chelated with 3 mM EGTA to totally quench the fura-2 signal and obtain $F_{min}$.

When quin-2- was used, cells were incubated with 10 uM quin-2- at 37° C. for 1 hour, washed and then used.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., *Clin Pharmacol Ther* (1974) 16:900–904].

Inhibition of Phospholipase $A_2$

The effect of compounds of this invention on bee venom phospholipase $A_2$ is determined by the following procedure:

a. Bee venom phospholipase $A_2$ in 10 uM HEPES (pH 7.4) with 1 mM $CaCl_2$ is incubated with vehicle or test agent for 1.0 hour at 41°.
b. 1.36 mM phosphotidylcholine, 2.76 mM Triton X-100 are dispersed in buffer by sonication and then mixed with L-3 phosphotidylcholine, 1-palmitoyl-2-(1-$^{14}$C) palmitoyl for 10 min.
c. Start the reaction by the addition of enzyme (0.495 units/ml).
d. Incubation for 15 sec. at 41°.
e. Reaction is terminated by addition of 2.5 ml of isopropanol: n-heptane: 0.5 M $H_2SO_4$ (40:10:1; v:v:v:).
f. 2.0 ml n-heptane and 1.0 ml $H_2O$ added; mixture centrifuged.
g. 2.0 n-heptane removed and treated with 200–300 mg of silica gel HR60.
h. Samples centrifuged; 1 ml of n-heptane SN removed and added to 10 ml scintillation fluid.
i. Samples counted on a scintillation counter.

Inhibition of Phosphoinositide-specific Pholicase C

The effect of compounds of this invention on phosphoinositide-specific phospholipase C may be determined by procedures described by Bennett et al, *Molecular Pharmacology* 32:587–593 (1987).

Activity Data

In the above-described phospholipase $A_2$ assay the compounds of the invention were found to provide 50% inhibition ($IC_{50}$) of bee venom phospholipase $A_2$ at the following concentrations (in micromoles), as indicated in Table 1.

TABLE 1

| Phospholipase $A_2$ Assay. | |
|---|---|
| Compound name or number | $IC_{50}$ (um) |
| 1* | 0.03 |
| 7 | 0.26 |
| 8 | 0.09 |
| 9 | 0.42 |
| 10 | >1 |
| 11 | 0.08 |
| 12 | 0.13 |
| 13 | 0.1 |
| 23 | 0.04 |
| 24 | 0.08 |

*Data for Compound 1 (monoalide) are provided for comparison.

The compounds of the present invention can be made by the synthetic chemical pathways which are illustrated above in general terms, and in the specific examples as well. The synthetic chemist will readily appreciate that the conditions described here in general terms, and specifically, can be generalized to any and all compounds represented by Formula 1 or by Formula 2, as applicable. Furthermore, the synthetic chemist will readily appreciate that the herein described synthetic steps may be varied or adjusted by those skilled in the art without departing from the scope and spirit of the invention. Therefore, the following examples of specific compounds of the invention, and specific examples of the synthetic steps in which the compounds and certain intermediates are made, are set out to illustrate the invention, not to limit its scope.

SPECIFIC EXAMPLES

Example 1

2-Trimethylsilyl-4-furaldehyde (Compound 4)

n-Butyl lithium (a 2.5 M solution in hexane; 28.8 ml, 72 mmol) was added to a solution of morpholine (6.28 ml, 72 mmol) in tetrahydrofuran (700 ml) at −78° under argon. After 20 minutes, 3-furaldehyde (7.0 g, 72 mmol) was added. After another 20 minutes, sec-butyl lithium (a 1.3 M solution in cyclohexane; 55.4 ml, 72 mmol) was added dropwise and stirring continued at −78° for 7 hours before trimethylsilyl chloride (27 ml, 216 mmol) was added. Stirring was continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with diethyl ether. All the organic phases were combined, dried (magnesium sulfate) and evaporated to dryness to give a light brown oil, which was purified by flash chromatography on silica using 2% ethyl ether/hexane. Fractions with $R_f$ of about 0.30 (silica, 10% ethyl ether/hexane) on evaporation gave the title aldehyde as a light yellow oil, b.p. 48–50°/0.25 torr.

$^1$H NMR (CDCl$_3$) 0.29 (s, 9H), 6.98 (s, 1H), 8.25 (s, 1H) and 9.95 (s, 1H).

$^{13}$C NMR (CDCl$_3$) −2.0, 116.2, 128.9, 155.3, 164.1 and 184.5.

HRMS exact mass calculated for $C_8H_{12}O_2Si(M^+)$ 168.0607, found 168.0588.

4-(1-Hydroxytridecyl)-2-trimethylsilylfuran (Compound 25)

A solution of 2-trimethylsilyl-4-furaldehyde (0.5 g, 2.97 mmol) in tetrahydrofuran (5 ml) was added to a solution of dodecyl magnesium bromide (5.95 mmol; prepared from 1.48 g dodecyl bromide and 146 mg magnesium turnings in 30 ml tetrahydrofuran) at room temperature. After 2 hours, the mixture was quenched with ammonium chloride solution and extracted thoroughly with ethyl ether. Evaporation of the dried (magnesium sulfate) extracts gave an oil which was flash chromatographed on silica using 10% ethyl ether/hexane. Fractions with $R_f$ about 0.13 gave, after evaporation, the title alcohol as a pale yellow oil.

$^1$H NMR (CDCl$_3$): 0.26 (s, 9H), 0.89 (t, 3H, J=7.3 Hz), 1.27 (broad s, 16H), 1.62 (br, 1H), 1.75 (m, 2H), 4.65 (t, 1H, J=6.8 Hz), 6.63 (s, 1H) and 7.57 (s, 1H).
LRMS m/e (% abundance): 293 ($M^+$−2), 221 (5), 177 (31), 175 (33), 97 (14), 87 (10), 85 (64), 83 (100), 73 (14) and 57 (12).

4-(1-Ketotridecyl)-2-trimethylsilylfuran (Compound 26)

A mixture of dimethyl sulfoxide (0.5 ml) and dichloromethane (5 ml) was added dropwise to a solution of oxalyl chloride (0.36 ml, 4.18 mmol) in dichloromethane (5 ml) at −78° under argon. After 5 minutes, a solution of 4-(1-hydroxytridecyl)-2-trimethylsilylfuran (Compound 25, 1.01 g, 2.98 mmol) in dichloromethane (5 ml), followed by triethylamine (1.66 ml, 11.9 mmol) after 20 minutes, was added. Stirring was continued for 3 hours while the cooling bath attained room temperature. The mixture was quenched with water and extracted with dichloromethane. The dried (magnesium sulfate) extracts on evaporation gave a residue which was purified by a silica column using 2.5% ethyl ether/hexane. Fractions with $R_f$ of about 0.27 (5% ethyl ether/hexane) on evaporation gave the titled ketone as an off-white solid.

$^1$HNMR (CDCl$_3$): 0.31 (s, 9H), 0.91 (t, 3H, J=7.0 Hz), 1.29 (br s, 18H), 1.75 (m, 2H), 2.75 (t, 2H, J=7.0 Hz), 6.99 (s, 1H) and 8.22 (s, 1H). LRMS (m/e, % abundance) 337[(M+H)+ 5], 336 (M+, 17), 183 (16), 182 (100), 167 (43) and 73 (23).

Ethyl 3-dodecyl-3-(2-trimethylsilyl-4-furyl)-2-propenoate (Compound 27)

A mixture of 4-(1-ketotridecyl)-2-trimethylsilylfuran (Compound 26, 84.5 mg, 0.25 mmol), zinc (100 mg, 1.53 mmol) and ethyl bromoacetate (105 mg, 0.63 mmol) in benzene (6 ml) was refluxed for 2 hours. After cooling to 0°, acetic anhydride (83 ul, 0.88 mmol) was added. Stirring was continued for 14 hours while the cooling bath attained room temperature. The mixture was washed with 5% sodium bicarbonate and water. Evaporation of the dried (magnesium sulfate) organic phase gave a residue which was purified by a silica column using 2% ethyl ether/hexane to give the title ester.

$^1$H NMR (CDCl$_3$): 0.27 (s, 9H), 0.88 (t, 3H, J=5.8 Hz), 1.25 (m, 18H), 1.30 t, 3H, J=7.1 Hz), 1.50 (m, 2H), 2.90 (t, 2H, J=7.9 Hz), 4.19 (q, 2H, J=7.1 Hz), 6.02 (s, 1H) 6.76 (s, 1 H) and 7.82 (s, 1H).

$^{13}$C NMR (CDCl$_3$): −1.8, 14.1, 14.4, 22.7, 29.4, 29.5, 29.7, 30.1, 31.0, 31.9, 59.6, 113.3, 117.4, 127.3, 145.9, 152.0, 162.3 and 166.0.

HRMS exact mass calculated for $C_{24}H_{42}O_3Si(M^+)$ 406.2903, found 406.2905.

Ethyl 3-dodecyl-3-(2-trimethylsilyl-4-furyl)propanoate (Compound 28)

A mixture of ethyl 3-dodecyl-3-(2-trimethylsilyl-4-furyl)-2-propenoate (Compound 27, 141 mg, 0.35 mmol) and platinum oxide (28 mg) in ethanol (5 ml) was stirred under hydrogen at room temperature for 2 days. After the solvent and the catalyst were removed, the residue was purified by a silica column using 2% ethyl ether/hexane to give the title ester.

$^1$H NMR (CDCl$_3$): 0.16 (s, 9H), 0.80 (t, 3H, J=6.7 Hz), 1.11 (t, 3H, J=7.1 Hz), 1.23 (m, 20H), 1.50 (m, 2H), 2.40 (m, 2H), 2.95 (m, 1H), 4.00 (q, 1H, J=7.1 Hz), 4.01 (q, 1H, J=7.2 Hz), 6.39 (s, 1H) and 7.33 (s, 1H).

$^{13}$C NMR (CDCl$_3$): −1.6, 14.1, 22.7, 27.1, 29.3, 29.5, 29.6, 31.9, 32.4, 35.5, 41.3, 60.2, 119.3, 127.6 142.9, 160.5 and 172.6.

HRMS exact mass calculated for $C_{24}H_{44}O_3Si(M^+)$ 408.3059, found 408.3047.

4-[1-(Ethoxycarbonylmethyl)tridecyl]-5-hydroxy-2(5H)-furanone (Compound 7)

A mixture of ethyl 3-dodecyl-3-(2-trimethylsilyl-4-furyl)propanoate (Compound 28, 55.6 mg, 0.14 mmol) and Rose Bengal (ca. 5 mg) in acetone (7 ml) was exposed to singlet oxygen at −78° for 2 hours. The residue, after solvent removal, was purified by preparative thin layer chromatography (TLC, silica plates developed with 20% ethyl acetate/hexane) to give the title furanone.

IR(CHCl$_3$): 3350 (br), 2920 and 1750.

$^1$H NMR (CDCl$_3$): 0.88 (t, 3H, J=6.6 Hz), 1.35 (m, 23H), 1.60 (m, 2H), 2.70 (m, 3H), 4.14 (q, 2H, J=7.0 Hz), 5.40 (br s, 1H), 5.87 (s, 1H), 6.01 (br s, 1H) and 6.12 (br s, 1H).

$^{13}$C NMR (CDCl$_3$): 14.1, 22.7, 27.1, 29.4, 29.5, 29.6, 31.9 33.3, 35.0, 36.0, 38.6, 39.2, 61.4, 61.7, 98.5, 99.9, 117.5, 19.6, 170.1, 170.6, 172.5, 172.8 and 173.4.

HRMS exact mass calculated for 369.2641, found 369.2629.

Example 2

2-(tert-Butyldimethylsilyl)-4-furaldehyde (Compound 6)

n-Butyl lithium (a 2.5 M solution) in hexane; 8.3 ml, 20.8 mmol) was added to a solution of morpholine (1.81 ml, 20 mmol) in tetrahydrofuran (100 ml) at −78° C. under argon. After 20 minutes 3-furaldehyde (1.8 ml, 20.8 mmol) was added. After another 15 minutes, sec-butyl lithium (a 1.3 M solution in cyclohexane; 16.8 ml, 21.9 mmol) was added dropwise and stirring continued at −78° C. for 1 hour before a solution of t-butyldimethylsilyl chloride (9.4 g, 62.4 mmol) in tetrahydrofuran (10 ml) was added. Stirring was continued overnight (16 hours) while the cooling bath was allowed to attain room temperature. The solution was poured into ice cold 10% (v/v) hydrochloric acid (40 ml) and after stirring at 0° for 10 minutes, the layers were separated. The aqueous phase was extracted with diethyl ether. All the organic phases were combined, dried (magnesium sulfate) and evaporated to dryness to give a brown oil, which was distilled under high vacuum to give the title aldehyde, boiling point 80°-5°/0.5 torr., m.p. 37-8.

$^1$H NMR (CDCl$_3$) 0.23 (s, 6H), 0.90 (s, 9H), 6.99 (s, 1H), 8.25 (s, 1H) and 9.94 (s, 1H).

$^{13}$C NMR (CDCl$_3$) 16.6, 26.1, 117.3, 128.8, 155.5, 162.7 and 184.5.

HRMS exact mass calculated for $C_{11}H_{18}O_2Si$ (M$^-$) 210.1076, found 210.1075.

4-(2-keto-3-propenyl)-2-tert-butyldimethylsilylfuran (Compound 29)

Potassium bis(trimethylsilyl)amide (a 0.5 M solution in toluene; 2.62 ml, 5.24 mmol) was added to a solution of dimethyl (2-oxopropyl)phosphonate (790 mg, 5.24 mmol) in tetrahydrofuran (6 ml) at 0° under argon. After 20 minutes, a solution of 2-tert-butyldimethylsilyl-4-furaldehyde (Compound 6, 1.0 g, 4.76 mmol) in tetrahydrofuran (1 ml) was added. Stirring was continued for 14 hours while the cooling bath attained room temperature. The mixture was quenched with methanol/water (1:1, 20 ml) and was extracted thoroughly with ethyl ether. Evaporation of the dried (magnesium sulfate) extracts gave a residue, which was purified by a silica column using 5% ethyl acetate/hexane to give the title ketone.

IR(CHCL$_3$): 2940, 1650, 1610, 1355 and 1250.

$^1$H NMR (CDCl$_3$): 0.22 (s, 6H), 0.90 (s, 9H), 2.30 (s, 3H), 6.40 (d, 1H, J=16.1 Hz), 6.79 (s, 1H), 7.42 (d, 1H, J=16.1 Hz) and 7.85 (s, 1H).

$^{13}$C NMR (CDCl$_3$): 16.6, 26.2, 27.3, 117.9, 122.6, 133.5, 149.2, 161.7 and 198.1.

HRMS exact mass calculated for C$_{14}$H$_{22}$O$_2$Si(M$^+$) 250.1389, found 250.1383.

Dodecyl Cu(CN)ZnI (Compound 30)

A mixture of zinc (1.7 g, 26 mmol) and ethylene dibromide (a few drops) in tetrahydrofuran (2 ml) was warmed at 65° under argon for 1 minute. On cooling to room temperature, chlorotrimethylsilane (0.1 ml, 0.78 mmol) was added. After 15 minutes, the mixture was warmed to 30° and a solution of 1-iodododecane (6.17 ml, 25 mmol) in tetrahydrofuran (10 ml) was added. Stirring was continued at 40°-5° for 24 hours. The mixture was cannulated to a mixture of copper (I) cyanide (1.98 g, 22 mmol) and lithium chloride (1.9 g, 44 mmol; previously dried at 170° for 1 hour) at −10°. After stirring at 0° for 0.5 hours, the cuprate was ready to use.

4-[1-(2-oxopropyl)tridecyl]-2-tert-butyldimethylsilylfuran (Compound 31)

A solution of dodecylCu(CN)ZnI (Compound 30, 3.55 mmol) in tetrahydrofuran was added to a solution of 4-(2-keto-3-propenyl)-2-tert-butyldimethylsilylfuran (522 mg, 2.09 mmol) and chlorotrimethylsilane (0.79 ml, 6.23 mmol) in tetrahydrofuran (15 ml) at −60° under argon. After 2 hours at −60° the mixture was stirred at room temperature for 14 hours. The solution was quenched with saturated ammonium chloride and extracted with ethyl ether. The extracts were combined and washed with 5% sodium bicarbonate and water. Evaporation of the dried (magnesium sulfate) extract gave an oil, which was purified by a silica column using 2% ethyl ether/hexane to give the title ketone.

IR(CDCl$_3$): 2920, 1705 and 1250.

$^1$H NMR (CDCl$_3$): 0.22 (s, 6H), 0.91 (m, 12 H), 1.27 (m, 20 H), 1.50 (m, 2H), 2.07 (s, 3H), 2.63 (d, 2H, J=7.2 Hz), 3.09 (m, 1H), 6.50 (s, 1H) and 7.41 (s, 1H).

$^{13}$C NMR (CDCl$_3$): −6.7, 13.8, 16.5, 22.5, 26.1, 27.0, 29.2, 9.3, 29.4, 30.4, 31.2, 31.7, 35.5, 50.2, 120.5, 127.9, 143.3, 159.5 and 208.5.

HRMS exact mass calculated for C$_{26}$H$_{48}$O$_2$Si 420.3424, found 420.3416.

4-[1-(2-oxopropyl)tridecyl]-5-hydroxy-2(5H)-furanone (Compound 8)

A mixture of 4-[1-(2-oxopropyl)tridecyl]-2-tert-butyl-dimethylsilylfuran (Compound 31, 71.0 mg, 0.17 mmol), Rose Bengal (ca, 5 mg) and water (1 drop) in tetrahydrofuran (15 ml) was exposed to singlet oxygen at 0° for 1 hour. The residue, after solvent removal, was purified by a silica column using 30% ethyl acetate/hexane to give the title furanone.

IR (CDCl$_3$): 3400, 2930, 1755 and 1710.

$^1$H NMR (CDCl$_3$): 0.88 (t, 3H, J=6.7 Hz), 1.25 (m, 20H), 1.52 (m, 2H), 2.19 (s, 3H), 2.85 (br m, 3H), 5.80 (s, 1H) and 6.00 (br m, 2H).

$^{13}$C NMR (CDCl$_3$): 13.8, 22.4, 26.9, 29.0, 29.1, 29.3, 29.4, 29.8, 31.7, 32.2, 34.5, 48.5, 99.9, 117.3, 171.2, 173.2 and 209.6.

HRMS exact mass calculated for C$_{20}$H$_{35}$O$_4$ (M+H)$^+$ 339.2535, found 339.2548.

Example 3

4-[1-(2-Hydroxy-2-methylpropyl)tridecyl]-2-tert-butyldimethylsilylfuran (Compound 32)

A mixture of methylmagnesium chloride (a 3 M solution in tetrahydrofuran; 0.68 ml, 2.04 mmol) and 4-[1-(2-oxopropyl)tridecyl]-2-tert-butyldimethylsilylfuran (Compound 31, 429 mg, 1.02 mmol) in tetrahydrofuran (3 ml) was stirred at 0° at room temperature for 6 hours. The mixture was quenched with saturated ammonium chloride and extracted with ether. Evaporation of the dried (magnesium sulfate) extracts gave an oil, which was chromatographed on a silica column using 5% ethyl acetate/hexane to give the title alcohol.

IR (CHCl$_3$): 3550, 2920 and 2520.

$^1$H NMR (CDCl$_3$): 0.21 (s, 6H), 0.89 (m, 12H), 1.14 (s, 3H), 1.16 (s, 3H), 1.26 (m, 20 H), 1.40 (s, 1H), 1.50 (m, 2H), 1.75 (m, 2H), 2.70 (m, 1H), 6.52 (s, 1H), and 7.44 (s, 1H).

$^{13}$C NMR (CDCl$_3$): −6.7, 13.9, 16.6, 22.5, 26.1, 27.0, 29.2, 29.3, 29.4, 29.5, 30.1, 31.4, 31.7, 38.1, 49.1, 71.3, 120.4, 129.2, 143.4 and 160.2.

HRMS exact mass calculated for C$_{27}$H$_{52}$O$_2$Si(M$^+$) 436.3737, found 436.3739.

4-[1-(2-Hydroxy-2-methylpropyl)tridecyl]-5-hydroxy-2(5H)-furanone (Compound 10)

A mixture of 4-[1-(2-hydroxy-2-methylpropyl)-tridecyl]-2-tert-butyl-dimethylsilylfuran (Compound 32, 108 mg, 0.25 mmol), water (5 drops) and Rose Bengal (ca. 5 mg) was stirred at 0° for 1 hour. The residue, after solvent removal, was purified by a silica column using 60% ethyl acetate/hexane to give the title furanone.

IR (CHCl$_3$): 3400 and 1740.

$^1$H NMR (CDCl$_3$): 0.88 (t, 3H, J=6.3 Hz), 1.25 (m, 20 H), 1.29 (d, 3H, J=3.3 Hz), 1.31 (d, 3H, J=6.0 Hz), 1.48 (m, 2H), 1.60 (s, 1H), 1.65 (dd, 1H, J=4.2 Hz, 1.5 Hz), 1.82 (dd, 1H, J=14.3 Hz, 2.3 Hz), 1.92 (dd, 1H, J=14.1 Hz, 10.8 Hz), 2.23 (dd, 1H, J=14.7 Hz, 12.3 Hz), 2.57 (m, 1H), 2.89 (m, 1H), 5.82 (d, 1H, J=0.9 Hz), 5.86 (dd, 1H, J=1.2 Hz, 0.5 Hz), 5.90 (d, 1H, J=0.9 Hz), 5.93 (d, 1H, J=1.2 Hz), 6.00 (s, 1H), 6.03 s, 1H), 7.02 (d, 1H, J=3.8 Hz) and 7.06 (d, 1H, J=4.1 Hz).

$^{13}$C NMR (CDCl$_3$): 13.8, 22.4, 26.0, 26.5, 27.2, 29.1, 29.2, 29.3, 29.4, 31.4, 31.7, 32.4, 33.3, 34.6, 36.9, 37.3, 44.9, 51.5, 71.9, 99.2, 101.7, 116.4, 119.7, 172.7 and 178.1.

HRMS exact mass calculated for C$_{21}$H$_{42}$NO$_4$ (M+NH$_4$)$^-$ 372.3119 found 372.3112.

Example 4.

4-[1-(2-carboxymethyl)tridecyl]-2-trimethylsilylfuran (Compound 33)

A mixture of ethyl 3-dodecyl-3-(2-trimethylsilyl-4-furyl)propanoate (Compound 28, 133.5 mg, 0.33 mmol) and potassium hydroxide (73.3 mg, 1.31 mmol) in 95% ethanol (7 ml) was stirred at room temperature for 16 hours. After most of the solvent was removed, the residue was acidified with 10% hydrochloric acid and extracted thoroughly with ethyl ether. Evaporation of the dried (magnesium sulfate) extracts gave an oil, which was purified by a silica column using 20% ethyl acetate/hexane to give the titled acid.

IE (CHCl$_3$) 3400–2400, 2930, 1705 and 845.

$^1$H NMR (CDCl$_3$): 0.22 (s, 9H), 0.85 (t, 3H, J=6.2 Hz), 1.25 (m, 20 H), 1.52 (m, 2H), 2.52 (m, 2H), 30.4 (m, 1H), 6.38 (s, 1H) and 7.39 (s, 1H).

$^{13}$C NMR (CDCl$_3$): −1.9, 13.9, 22.5, 26.9, 29.2, 29.3, 29.4, 29.5, 31.8, 31.9, 35.3, 40.8, 119.3, 127.6, 143.2, 161.1 and 179.1

HRMS exact mass calculated for C$_{22}$H$_{40}$O$_3$Si(M$^+$) 380.2747 found 380.2744.

4-[1-(Carboxymethyl)tridecyl]-5-hydroxy-2(5H)-furanone (Compound 12)

A mixture of 4-[1-(carboxymethyl)tridecyl]-2-trimethylsilylfuran (Compound 33, 147 mg, 0.39 mmol), water (a few drops) and Rose Bengal (ca. 5 mg) in tetrahydrofuran (30 ml) was exposed to singlet oxygen at 0° for 2 hours. The residue, after solvent removal, was purified by chromatography on a silica column using 50% ethyl acetate/hexane to give the title furanone.

IR (CHCl$_3$) 3200, 2920, 1735 and 1705.

$^1$H NMR (CDCl$_3$): 0.88 (t, 3H, J=6.7 Hz), 1.31 (m, 22H), 1.62 (m, 2H), 2.71 (m, 2H), 2.99 (m, 1H), 5.92 (s, 2H), 6.04 (s, 1H), and 6.16 (s, 1H).

$^{13}$C NMR (CDCl$_3$) 14.1, 22.6, 26.8, 27.1, 29.3, 29.4, 29.6, 31.9, 33.2, 33.8, 34.1, 35.1, 37.8, 38.1, 99.1, 99.7 117.6, 119.0, 171.2, 171.9, 172.1, 172.2, 176.6 and 176.7.

HRMS exact mass calculated for C$_{19}$H$_{36}$NO$_5$(M+NH$_4$)$^+$ 358.2593 found 358.2592.

Example 5

Methyl 2-carbomethoxy-3-(2-trimethylsilyl-4-furyl)-2-propenoate (Compound 34)

A mixture of 2-trimethylsilyl-4-furaldehyde (Compound 4, 492 mg, 2.93 mmol), dimethyl malonate (774 mg, 86 mmol), piperidine (5 drops) and acetic acid (5 drops) in tetrahydrofuran (5 ml) was stirred at room temperature for 5 days. After most of the volatile residue was removed under high vacuum, the residual solid was recrystallized from hexane/diethyl ether to give the title diester.

IR (CHCl$_3$): 1705 and 1625

$^1$H NMR (CDCl$_3$): 0.25 (s, 9H), 3.81 (s, 3H), 3.89 (s, 3H), 6.51 (s, 1H), 7.64 (s, 1H) and 7.92 (s, 1H).

$^{13}$C NMR (CDCl$_3$): 1.9, 52.4, 52.5, 117.8, 120.2, 122.8, 133.7, 151.1, 163.3, 164.7 and 167.2.

HRMS exact mass calculated for C$_{13}$H$_{18}$O$_5$Si(M$^+$) 282.0923, found 282.0929.

4-[1,1-Bis(carbomethoxy)methyl)tridecyl]-2-trimethylsilylfuran (Compound 35)

A mixture of methyl 2-carbomethoxy-3-(2-trimethylsilyl-4-furyl)-2-propenoate (Compound 34, 434 mg, 1.54 mmol) and chlorotrimethylsilane (0.78 ml, 6.16 mmol) in tetrahydrofuran (2 ml) was added to a solution of dodecylCu(CN)ZnI (3.08 mmol) in tetrahydrofuran (6 ml) at −40° under argon. Stirring was continued at −10° for 16 hours. The mixture was quenched with saturated ammonium chloride and extracted with ethyl ether. Evaporation or the dried (magnesium sulfate) extracts gave an oil, which was purified by a silica column using 5% ethyl acetate/hexane to give the title diester.

IR (CHCl$_3$): 2925 and 1735.

$^1$H NMR (CDCl$_3$): 0.19 (s, 9H), 0.84 (t, 3H, J=6.7 Hz), 1.20 (m, 20 H), 1.50 (m, 2H), 3.28 (dt, 1H, J=9.8 Hz, 4.5 Hz), 3.48 (d, 1H, J=9.8 Hz), 3.50 (s, 3H), 3.71 (s, 3H), 6.41 (s,3H) and 7.39 (s, 1H).

$^{13}$C NMR (CDCl$_3$) −1.7, 14.1, 22.6, 27.0, 29.2, 29.3, 29.5, 29.6, 31.9, 33.0, 35.9, 52.1, 52.4, 58.2, 119.1, 124.2, 144.2, 160.6, 168.5 and 168.8.

HRMS exact mass calculated for C$_{25}$H$_{44}$O$_5$S(M$^+$) 452.2958, found 452.2954.

4-[-(1,1-Bis(carbomethoxy)methyl)tridecyl]-5-hydroxy-2(5H)-furanone (Compound 11)

A mixture of 4-[1-(1,1-bis(carbomethoxy)methyl)-tridecyl]-2-trimethylsilylfuran (Compound 25, 476 mg, 1.05 mmol), water (a few drops) and Rose Bengal (5 mg) in tetrahydrofuran (20 ml) was exposed to singlet oxygen at 0° for 2 hours. The residue, after solvent removal, was purified by chromatography on a silica column using 20% ethyl acetate/hexane to give the title furanone.

IR (CHCl$_3$): 3400, 1745 and 1730.

$^1$HNMR (CDCl$_3$): 0.88 (t, 3H, J=6.7 Hz), 1.32 (m, 20H), 1.60 (m, 2H), 3.22 (m, 1H), 3.37 (m, 1H), 3.73 (m, 1H), 3.73 (s, 3H), 3.75 (s, 3H), 3.80 (s, 3H), 3.81 (3H), 4.84 (d, 1H, J=10.7 Hz), 5.47 (d, 1H J=11.2 Hz), 5.88 (s, 1H), 5.94 (s, 1H), 5.98 (d, 1H, J=11.2 Hz) and 6.09 (d, 1H, J=10.3 Hz).

$^{13}$C NMR (CDCl$_3$): 14.0, 22.6, 26.6, 26.9, 29.1, 29.2, 29.4, 29.5, 31.4, 31.8, 32.6, 36.5, 38.4, 52.9, 53.0, 53.4, 55.3, 55.9, 98.5, 100.0, 118.6, 121.0, 167.8, 168.0, 169.4, 169.5 and 170.2.

HRMS exact mass calculated for C$_{22}$H$_{37}$O$_7$(M+H)$^+$ 413.2539 found 413.2529.

Example 6

4-(2,2-Dibromo-1-ethenyl)-2-trimethylsilylfuran (Compound 36)

A solution of 2-trimethylsilyl-4-furaldehyde (Compound 4, 1.0 g, 5.95 mmol) in dichloromethane (2 ml) was added to a solution of triphenylphosphine (3.9 g, 14.9 mmol) and carbon tetrabromide 2.46 g, 7.44 mmol) in dichloromethane (15 ml) at 0° under argon. After 1 hour, the mixture was extracted thoroughly with pentane. Evaporation of the pentane extracts gave an oil, which was flash chromatographed on silica using hexane. Fractions with R$_f$ of about 0.52 on evaporation gave the title silylfuran as a yellow oil.

$^1$H NMR (CDCl$_3$): 0.31 (s, 9H), 6.98 (s, 1H), 7.30 (s, 1H) and 8.04 (s, 1H).

LRMS m/e (% abundance): 322/324/326 (M$^+$, 32, 63, 33), 307/309/311(50, 100, 52), 252(15), 228/230(66, 68), 137/139(40,41) and 73(68).

4-[(3-Oxo-4,4,4-trifluoro)-1-butynyl]-2-trimethylsilylfuran (Compound 37)

n-Butyl lithium (a 1.6 M solution in hexane; 1.24 ml, 2 mmol) was added dropwise to a solution of 4-(2,2-dibromo-1-ethenyl)-2-trimethylsilylfuran (Compound 36, 296 mg, 0.91 mmol) in tetrahydrofuran (1 ml) at −78° under argon. After 1.5 hours, a solution of ethyl trifluoroacetate (0.32 ml, 2.72 mmol) in tetrahydrofuran (2 ml), followed by boron trifluoride etherate (0.25 ml, 2.72 mmol) wa added. After stirring at −78° for 14 hours, the mixture was quenched with saturated ammonium chloride and extracted with ethyl ether. Evaporation of the dried (magnesium sulfate) extracts gave an oil, which was purified by bulb to bulb distillation at room temperature under high vacuum to give the title alkyne.

IR (CHCl$_3$) 2200 and 1695.

$^1$H NMR (CDCl$_3$): 0.28 (s, 9H), 6.77 (s, 1H) and 8.15 (s, 1H).

$^{13}$C NMR (CDCl$_3$) −2.0, 86.9, 94.3, 103.9, 144.9, 121.5, 155.3, 163.4 and 166.8.

HRMS exact mass calculated for C$_{11}$H$_{12}$F$_3$O$_2$(M+) 261.0559, found 261.0550.

(E),(Z)-4-[(1-Dodecyl-3-oxo-4,4,4-trifluoro)-1-butenyl]-2-trimethylsilylfuran (Compound 38)

A solution of 4-[(3-oxo-4,4,4-trifluoro)-1-butynyl]-2-trimethylsilylfuran (Compound 37, 891 mg, 3.43 mmol) and chloromethylsilane (1.31 ml, 10.3 mmol) in tetrahydrofuran (5 ml) was added to a solution of dodecyl-Cu(CN)ZnI (Compound 30, 3.43 mmol) in tetrahydrofuran (5 ml) at −78° under argon. Stirring was continued at −40° for 16 hours, thereafter the mixture was quenched with saturated ammonium chloride and extracted with ether. Evaporation of the dried (magnesium sulfate) extracts gave an oil, which was purified by chromatography on a silica column using 1% ethyl ether/hexane to give the title furan.

IR (CHCl$_3$): 2930, 1695 and 1575.

$^1$H NMR (CDCl$_3$): 0.30 (s, 9H), 0.31 (s, 9H), 0.89 (t, 3H, J=6.4 Hz), 1.35 (m, 18H), 1.58 (m, 2H), 2.61 (t, 1H, J=7.7 Hz), 2.94 (t, 1H, J=7.6 Hz), 6.38 (s, 1H), 6.62 (s, 1H), 6.84 (s, 1H), 6.88 (s, 1H), 8.04 (s, 1H) and 8.68 (s, 1H).

$^{13}$C NMR (CDCl$_3$): −1.84, −1.95, 14.1, 22.7, 29.3, 29.4, 29.5, 29.6, 29.7, 30.1, 31.9, 32.3, 32.5, 40.8, 111.1, 113.4, 116.4, 116.6, 119.8, 122.6, 127.5, 148.7, 151.5, 161.0, 161.9, 158.9, 163.7, 177.6 and 179.1

HRMS exact mass calculated for C$_{23}$H$_{37}$F$_3$O$_2$S(M+) 430.2515, found 430.2498.

4-[1-(3,3,3-Trifluoro-2-oxo)propyl]tridecyl-2-trimethylsilylfuran (Compound 39)

A solution of (E)-(Z)-4-[(1-dodecyl-3-oxo-4,4,4-trifluoro)-1-butenyl]-2-trimethylsilylfuran (Compound 38, 8.7 mg, 0.02 mmol) in ethyl acetate (2 ml) was hydrogenated over 10% palladium on carbon at room temperature for 3 hours. The solution was evaporated to dryness and thereafter, was purified by chromatography on a silica column using 1% ethyl ether/hexane to give the title furan.

$^1$H NMR (CDCl$_3$): 0.22 (s, 9H), 0.85 (t, 3H, J=6.8 Hz), 1.22 (m, 20H), 1.50 (m, 2H), 2.87 (d, 2H, J=7.0 Hz), 3.15 (m, 1H), 6.42 (s, 1H) and 7.39 (s, 1H).

$^{13}$C NMR (CDCl$_3$): −1.68, 14.1, 22.7, 27.1, 29.3, 29.4, 29.5, 29.6, 30.0, 31.9, 35.3, 43.1, 115.4, 118.7, 126.7, 143.1, 161.2 and 190.3.

HRMS exact mass calculated for C$_{23}$H$_{39}$F$_3$O$_2$Si(M+) 432.2671, found 432.2660.

4-[1-(3,3,3-Trifluoro-2-oxo)propyl]tridecyl-5-hydroxy-2(5H)-furanone (Compound 9)

A mixture of 4-[1-3,3,3-trifluoro-2-oxo)propyl]tridecyl-2-trimethylsilylfuran (Compound 39, 56 mg, 0.13 mmol), water (a few drops) and Rose Bengal (5 mg) in acetone (3 ml) was exposed to singlet oxygen at −65° for 6 hours. The residue, after solvent removal, was purified by chromatography on preparative silica plates (developed with 20% ethyl acetate/hexane) to give the title furanone.

IR (CHCl$_3$): 3400, 2900 and 1770

$^1$HNMR (CDCl$_3$): 0.88 (t, 3H, J=6.7 Hz), 1.40 (m, 22H), 2.35 (dd, 1H, J=13.2 Hz, 5.7 Hz), 3.03 (m, 1H), 4.10 (br s, 1H), 5.88 (s, 1H), 5.89 (s, 1H) and 6.08 (s, 1H).

$^{13}$C NMR·(CDCl$_3$): 13.8, 22.5, 26.1, 29.1, 29.2, 29.3, 29.4, 31.2, 31.7, 32.4, 34.9, 96.2, 96.8, 113.9, 121.8, 169.2 and 170.6.

HRMS exact mass calculated for C$_{20}$H$_{31}$F$_3$O$_4$(M+) 392.2174, found 392.2169.

Example 7

(E),(Z)-4-[(1-Dodecyl-3-oxo-4,4,4-trifluoro)-1-butenyl]-5-hydroxy-2(5H)-furanone (Compound 23)

A mixture of (E),(Z)-4-[(1-dodecyl-3-oxo-4,4,4-trifluoro)-1-butenyl]-2-trimethylsilylfuran (Compound 38, 83.9 mg, 0.19 mmol) water (two drops) and Rose Bengal (5 mg) in tetrahydrofuran (5 ml) was added to singlet oxygen at −78° for 2 hours. The residue, after solvent removal, was purified by chromatography on a silica column using 30% ethyl acetate/hexane to give the title furanone.

IR (CHCl$_3$): 3200, 2930 and 1780

$^1$HNMR (CDCl$_3$): 0.88 (t, 3H, J=6.7 Hz), 1.45 (m, 20H), 1.42 (m, 20H), 2.41 (t, 3H, J=6.8 Hz), 2.85 (m, 1H), 4.0 (br, 1H), 4.65 (br s, 1H), 5.92 (s, 1H), 6.05 (s, 1H), 6.22 (s, 1H), 6.40 (s, 1H), 6.49 (s, 1H) and 6.88 (s, 1H).

$^{13}$C NMR (CDCl$_3$): 13.8, 22.5, 27.1, 28.8, 29.0, 29.1, 29.3, 29.4, 29.7, 30.9, 31.6, 31.7, 94.6, 95.3, 97.6, 97.7, 114.1, 115.8, 120.1, 121.6, 123.8, 124.0, 138.0, 138.6, 155.3, 157.1, 157.5, 161.8, 170.0 and 180.4.

HRMS exact mass calculated for C$_{20}$H$_{29}$F$_3$O$_4$(M+) 390.2018, found 390.2023.

Diethyl [2-trimethylsilyl-4-(1-ethynyl]furylphosphonate (Compound 40)

n-BuLi (a 1.6 M solution in hexane; 2.03 ml, 3.24 mmol) was added dropwise to a solution of 4-(2,2-dibromo-1-ethenyl)-2-trimethylsilylfuran (Compound 36, 480 mg, 1.47 mmol) in tetrahydrofuran (2 ml) at −78° under argon. After 30 minutes, diethyl chlorophosphate (0.64 ml, 4.42 mmol) was added. Stirring was continued at −78° for 1 hour and at room temperature for 30 minutes. The mixture was quenched with water and extracted with ether. The extracts were combined, washed with 5% sodium bicarbonate and water. Evaporation of the dried (magnesium sulfate) extracts gave an oil, which was purified by chromatography on a silica column using 20% ethyl acetate/hexane to give the title alkyne.

IR (CHCl$_3$): 2980 and 2180.

$^1$H NMR (CDCl$_3$): 0.21 (s, 9H), 1.33 (t, 6H, J=7.1 Hz), 4.15 (dq, 4H, J=9.0 Hz, 7.7 Hz), 6.64 (s, 1H) and 7.92 (s, 1H).

$^{13}$C NMR (CDCl$_3$): −2.3, 15.8, 15.9, 63.0, 63.1, 82.6, 91.6, 92.3, 104.7, 121.5, 121.6, 152.8, 152.9 and 162.4.

HRMS exact mass calculated for C$_{13}$H$_{21}$O$_4$PSi(M+) 300.0946, found 300.9033.

(E),(Z)-Diethyl 2-[2-dodecyl-2-(2-trimethylsilyl-4-furyl)]ethenylphosphonate (Compound 41)

A mixture of diethyl [2-trimethylsilyl-4-(1-ethynyl)]furylphosphonate (Compound 40, 238 mg, 0.79 mmol) and chlorotrimethylsilane (0.3 ml, 2.38 mmol) in tetrahydrofuran (2 ml) was added to a solution of dodecyl-Cu(CN)ZnI (Compound 30, 0.95 mmol) in tetrahydrofuran (2 ml) at −78° under argon. After 3 hours at −20°, the mixture was quenched with water and extracted with ethyl ether. Evaporation of the dried (magnesium sulfate) extracts gave an oil, which was purified by a silica column using 40% ethyl acetate/hexane to give the title furan.

IR(CHCl$_3$): 2930, 1605 and 1240.

$^1$H NMR (CDCl$_3$): 0.29 (s, 9H), 0.84 (t, 3H, J=6.7 Hz), 1.25 m, 18H), 1.30 (t, 6H), J=7.1 Hz), 1.52 (m, 2H), 2.73 (dt, 2H, J=2.2 Hz, 3.9 Hz), 4.06 (dq, 4H, J=7.3 Hz, 7.1 Hz), 5.67 (d, 1H, J=16.1 Hz), 6.69 (s, 1H) and 7.74 (s, 1H).

$^{13}$C NMR (CDCl$_3$): −1.8, 14.1, 16.3, 16.4, 22.7, 29.3, 29.4, 29.6, 30.0, 30.2, 31.9, 32.7, 32.8, 61.2, 61.3, 108.2, 110.8, 117.6, 126.8, 127.2, 145.3, 154.3, 154.5 and 162.1.

HRMS exact mass calculated for C$_{25}$H$_{47}$O$_4$PSi(M+) 470.2981, found 470.2971.

Diethyl 2-[2-dodecyl-2-(2-trimethylsilyl-4-furyl)]ethylphosphonate (Compound 42)

A solution of (E),(Z)-diethyl 2-[2-dodecyl-2-(2-trimethylsilyl-4-furyl-ethenylphosphonate (Compound 41, 24 mg, 0.05 mmol) in ethyl acetate (2 ml) was hydrogenated over platinum (IV) oxide (3 mg) at room temperature for 16 hours. After most of the solvent was removed, the residue was purified by chromatography on a silica column using 30% ethyl acetate/hexane to give the title furan.

IR (CHCl$_3$): 2920, 1220, 1050 and 1020.

$^1$H NMR (CDCl$_3$): 0.20 (s, 9H), 0.84 (t, 3H, J=6.7 Hz), 1.21 (m, 26H), 1.46 (m, 1H), 1.71 (m, 1H), 1.97 (m, 2H), 2.94 (m, 1H) 3.86 (m, 4H), 6.45 (s, 1H) and 7.42 (s, 1H), $^{13}$C NMR (CDCl$_3$): −1.9, 13.9, 16.0, 16.1, 22.5, 26.8, 29.1, 29.2, 29.3, 29.5, 29.9, 30.0, 31.6, 31.7, 33.5, 36.8, 37.0, 61.0 61.1, 61.2, 119.2, 128.1, 128.2, 143.4 and 160.9.

HRMS exact mass calculated for C$_{25}$H$_{49}$O$_4$pSi(M+) 472.3138, found 472.3132.

4-[1-(diethylphosphonyl)methyl]tridecyl-5-hydroxy-2(5H)-furanone Compound 13)

A mixture of diethyl 2-[2-dodecyl-2-(2-trimethylsilyl-4-furyl)]ethylphosphonate (Compound 42, 11.5 mg, 0.02 mmol), water (2 drops) and Rose Bengal (2 mg) in tetrahydrofuran (5 ml) was exposed to singlet oxygen at 0° for 4 hours. The residue, after solvent removal, was purified by a silica column using 20% ethyl acetate/hexane to give the titled furanone.

IR (CHCl$_3$): 3200, 2920, 1750, 1045 and 1020.

$^1$H NMR (CDCl$_3$): 0.88 (t, 3H, J=6.7 Hz), 1.30 (m, 26H), 1.60 (m, 2H), 2.12 (m, 2H), 2.77 (m, 1H), 3.00 (m, 1H), 2.59 (m, 4H), 5.90 (m, 2H), 7.16 (d, 1H, J=12.3 Hz) and 7.27 (d, 1H, J=10.5 Hz).

$^{13}$C NMR (CDCl$_3$): 13.9, 16.0, 16.1, 16.2, 22.5, 26.9, 27.1, 28.5, 29.0, 29.1, 29.2, 29.3, 29.4, 30.3, 31.2, 31.7, 31.8, 31.9, 33.1, 34.8, 34.9, 35.2, 35.4, 37.6, 37.9, 62.2, 62.3, 62.4, 62.6, 62.7, 98.3, 100.7, 118.6, 121.4, 168.5, 170.3, 170.8, 172.4 and 172.5.

HRMS exact mass calculated for C$_{22}$H$_{42}$O$_6$P(M+H)+ 433.2719, found 433.2715.

4-[(1-Dodecyl-2-diethylphosphonyl)-1-ethenyl]-5-hydroxy-2(5H)-furanone (Compound 24)

A mixture of (E),(Z)-diethyl 2-[2-dodecyl-2-(2-trimethylsilyl-4-furyl)]ethenylphosphonate (Compound 41, 38 mg, 0.08 mmol), water (2 drops) and Rose Bengal (5 mg) in tetrahydrofuran (5 ml) was exposed to singlet oxygen at 0° for 5 hours. The residue, after solvent removal, was purified by a silica column using 50% ethyl acetate/hexane to give the title furanone.

IR(CDCl$_3$): 3200, 2950, 1750, 1220, 1050 and 1020.

$^1$H NMR (CDCl$_3$): 0.88 (t, 3H, J=6.7 Hz), 1.25 (m, 18 H), 1.36 (t, 6H, J=7.1 Hz), 1.50 (m, 2H), 2.66 (m, 2H), 4.13 (dq, 4H, J=7.5 Hz, 7.1 Hz), 6.20 (s, 1H), 6.24 (d, 1H, J=15.8 Hz), 6.31 (d, 1H, J=7.2 Hz) and 7.24 (d, 1H, J=7.3 Hz).

$^{13}$C NMR (CDCl$_3$ ): 14.1, 16.3, 16.4, 22.7, 29.3, 29.4, 29.5, 29.6, 30.0, 31.9, 32.1, 32.2, 62.3, 62.4, 98.2, 120.3, 122.8, 150.9, 151.0, 161.6, 161.0 and 170.5.

HRMS exact mass calculated for C$_{22}$H$_{39}$O$_6$P(M+) 430.2484, found 430.2479.

Example 10

5-(2,4,5-Trifluorophenyl)-3-pentyn-1-ol (Compound 43)

A mixture of 1-bromo-2,4,5-trifluorobenzene (5.0 g, 23.7 mmol), 4-pentyn-1-ol (2.4 ml, 26 mmol), palladium bis(triphenylphosphine chloride (5 mg), copper (I) iodide (5 mg) in triethylamine (30 ml) was refluxed under argon for 10 hours. On cooling, the mixture was acidified with dilute hydrochloric acid and was extracted with ethyl ether. Evaporation of the extracts gave an oil, which was purified by chromatography on a silica column using 60% ethyl ether/hexane to give the title alcohol.

$^1$H NMR (CDCl$_3$): 1.55 (br, 1H), 1.89 (p, 2H, J=6.3 Hz), 2.59 (t, 2H, J=6.9 Hz), 3.84 (t, 2H, J=6.2 Hz,), 6.95 (m, 1H) and 7.20 (m, 1H).

LRMS (m/e, % abundance) 214 (M+, 47), 196(47), 195(77), 182(20), 177(20), 169(100), 168(10), 167(15), 158(38), 156(25), 145(35) and 133(16).

Reacting 5-(2,4,5-trifluorophenyl)-4-pentyn-1-ol (Compound 43) with methanesulfonyl chloride and sodium iodide gives 5-(2,4,5-trifluorophenyl)-1-iodo-4-pentyne. Treatment of this iodide with zinc and copper cyanide, as in Example 2, gives the corresponding mixed cuprate. Addition of this cuprate to 4-[(3-oxo-4,4,4-trifluoro)-1-butynyl]-2-trimethylsilylfuran (Compound 37) and hydrogenating the adduct gives 4-[1-(2-oxo-3,3,3-trifluoro)propyl-6-(2,4,5-trifluorophenyl)-]hexyl-2-trimethylsilylfuran (Compound 44). Oxidizing this furan (Compound 44) with singlet oxygen gives 4-[1-(2-oxo-3,3,3-trifluoro)propyl-6-(2,4,5-trifluorophenyl)]hexyl-5-hydroxy-2(5H)-furanone (Compound 14).

Example 11

2-Triethylsilyl-4-furaldehyde (Compound 5)

n-Butyl lithium (a 2.5 M solution in hexane; 30.6 ml, 76.5 mmol) was added to a solution of morpholine (6.66 ml, 76.5 mmol) in tetrahydrofuran (500 ml) at −78° under argon. After 15 minutes, 3-furaldehyde (6.3 ml, 72.8 mmol) was added. After another 20 minutes, sec-butyl lithium (a 1.3 M solution in cyclohexane; 59.0 ml, 76.5 mmol) was added dropwise and stirring continued at −78° for about 2 hours before triethylsilylchloride (13.4 ml, 80.1 mmol) was added. Stirring was continued overnight (14 hours) while the cooling bath was allowed to attain room temperature. The solution was poured into ice cold 10% (v/v) hydrochloric acid (100 ml) and after stirring at 0° for 10 minutes, the layers were separated. The aqueous phase was extracted with diethyl ether. All the organic phases were combined, dried (magnesium sulfate) and evaporated down to give an oil, which was distilled under high vacuum to give the 5-triethylsily-3-furaldehyde as a pale yellow oil, boiling point 85°-90°/0.4 torr.

IR (neat) 1680 cm$^{-1}$ $^1$H NMR (CDCl$_3$) 0.79 (q, 6H, J=7.3 Hz), 0.90 (t, 9H, J=7.3 Hz), 7.0 (s, 1H), 8.26 (s, 1H) and 9.95 (s, 1H).

13C NMR (CDCL₃) 2.9, 7.1, 117.2, 128.8, 155.6, 162.3 and 184.6.

HRMS m/e exact mass calculated for $C_{11}H_{18}O_2Si(M+)$ 210.1076, found 210.1071.

Reacting 2-triethylsilyl-4-furaldehyde (Compound 5) with (triphenylphosphoranylidene)acetaldehyde gives 3-(2-triethylsilyl-4-furyl)-2-propen-1-al (Compound 45). Conjugate addition of dodecylCu(CN)ZnI (Compound 30) to this aldehyde (Compound 45) gives 4-[1-(2-oxoethyl)tridecyl]-2-triethylsilylfuran (Compound 46). Treatment of this intermediate with manganese dioxide, sodium cyanide and ammonia in tert-butanol, followed by singlet oxygen oxidation gives 4-[1-(2-carboxyamido)methyl]tridecyl-5-hydroxy-2(5H)-furanone (Compound 16).

Example 12

Reacting 4-[1-(2-oxoethyl)tridecyl]-2-triethylsilylfuran (Compound 46) with N-methylhydrazine gives 4-[(1-N-methylhydrazinyl)ethyl]tridecyl-2-triethylsilylfuran (Compound 47). Oxidizing this intermediate (Compound 47) with singlet oxygen gives 4-[(1-N-methylhydrazinyl)ethyl]tridecyl-5-hydroxy-2(5H)-furanone (Compound 18).

Example 13

As in example 12, but substituting N-methylhydrazine with hydroxylamine and carry through the rection sequence gives 4-[1-(2-oximino)ethyl]tridecyl-5-hydroxy-2(5H)-furanone (Compound 17).

Example 14

Reacting 4-[1-(2-oxopropyl)]tridecyl-2-triethylsilylfuran with hydroxylamin gives 4-[1-(2-oximinopropyl)]-tridecyl-2-triethylsilylfuran (Compound 48). Oxidizing this intermediate with singlet oxygen gives 4-[1-(2-oximinopropyl)]tridecyl-5-hydroxy-2[5H]-furanone (Compound 22).

Example 15

As in Example 8, but substituting diethyl chlorophosphate with diethyl chlorothiophosphate and carrying through the reaction sequence to give 4-[1-(diethylthiophosphonyl)methyl]tridecyl-5-hydroxy-2(5H)-furanone (Compound 20).

Example 16

As in Example 8, but substituting diethyl chlorophosphate with methanesulfonyl chloride and carrying through the reaction sequence gives 4-[1-(methylsulfonyl)-methyl]tridecyl-5-hydroxy2(5H)-furanone (Compound 21).

Example 17

As in Example 6, but substituting ethyl trifluoroacetate with ethyl difluoroacetate and carrying through the reaction sequence gives 4-[1-(2-oxo-3,3-difluoro)-propyl]tridecyl-5-hydroxy-2(5H)-furanone (Compound 19).

What is claimed is:

1. A compound of the Formula

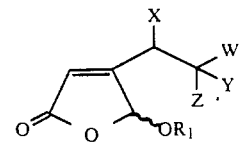

where
$R_1$ is H or alkyl of 1 to 20 carbons, $CO-R_1^*$, $CO-O-R_1^*$, $CO-NH-R_1^*$ or $PO(OR_1^*)_2$ or $PO(OR_1^*)R_1^*$ where $R_1^*$ independently is alkyl of 1 to 20 carbons, or phenyl;

X is long chain alkyl having 5 to 25 carbon atoms, long chain alkyl of 5 to 25 carbons substituted with an aryl group, or long chain alkyl of 5 to 25 carbons substituted with a fluoro substituted aryl group;

Y is COOH, COOR₂, CONH₂, CONHR₂, CON(R₂)₂, CHO, COR₂, COCF₃, COCHF₂, CH=NR₂, CR₂=N—R₂, CH=N—NHR₂, CH=N—N(R₂)₂, CH=NOH, CR₂=N—OH, CH=NOR₂, CR₂=NOR₂, CR₂=N—NHR₂, CR₂=N—N(R₂)₂, CH₂OH, CHR₂OH, C(R₂)₂OH, CH₂OR₂*, CHR₂OR₂*, C(R₂)₂OR₂*, SO₂R₂, PO(OR₃)₂, and PS(OR₃)₂, where R₂ independently is lower alkyl, or phenyl, R₂* is lower alkyl, phenyl, alkanoyl having 1 to 6 carbons, or aroyl, and R₃ is H, lower alkyl, or phenyl;

W is H, lower alkyl, phenyl, COOH, COOR₄, CONHR₄, CON(R₄)₂, where R₄ is lower alkyl, and Z is H or lower alkyl, or a pharmaceutically acceptable salt thereof.

2. A compound of claim 1 where $R_1$ is hydrogen or acyl.
3. A compound of claim 1 where $R_1$ is acetyl.
4. A compound of claim 1 where Z is hydrogen.
5. A compound of claim 1 where W is hydrogen.
6. A compound of claim 1 where W is COOR₄.
7. A compound of claim 1 where X is long chain alkyl having at least 5 carbon atoms.
8. A compound of claim 1 where X is long chain alkyl of 5 to 25 carbons substituted with an aryl group, or long chain alkyl of 5 to 25 carbons substituted with a fluoro substituted aryl group.
9. A compound of claim 1 where Y is COOH, COOR₂, CONH₂, COR₂; COCF₃, COCHF₂, CH=NOH, CR₂=N—OH, CH=NOR₂, CR₂=NOR₂, CH=N—NHR₂, CR₂=NHR₂, C(R₂)₂OH, SO₂R₂, PO(OR₃)₂, and PS(OR₃)₂.
10. A compound of claim 9 where R₂ is methyl or ethyl.
11. A compound of the Formula

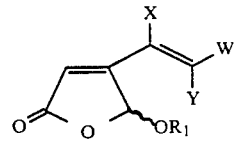

where $R_1$ is H or alkyl of 1 to 20 carbons, $CO-R_1^*$, $CO-O-R_1^*$, $CO-NH-R_1^*$ or $PO(OR_1^*)_2$ or $PO-(OR_1^*)R_1^*$ where $R_1^*$ independently is alkyl of 1 to 20 carbons, or phenyl;

X is long chain alkyl having 5 to 25 carbon atoms, long chain alkyl of 5 to 25 carbons substituted with an aryl group, or long chain alkyl of 5 to 25 carbons substituted with a fluoro substituted aryl group;

Y is $COOH$, $COOR_2$, $CONH_2$, $CONHR_2$, $CON(R_2)_2$, $CHO$, $COR_2$; $COCF_3$, $COCHF_2$, $CH=NR_2$, $CR_2=N-R_2$, $CH=N-NHR_2$, $CH=N-N(R_2)_2$, $CH=NOH$, $CR_2=N-OH$, $CH=NOR_2$, $CR_2=NOR_2$, $CR_2=N-NHR_2$, $CR_2=N-N(R_2)_2$, $CH_2OH$, $CHR_2OH$, $C(R_2)_2OH$, $CH_2OR_2^*$, $CHR_2OR_2^*$, $C(R_2)_2OR_2^*$, $SO_2R_2$, $PO(OR_3)_2$, and $PS(OR_3)_2$, where $R_2$ independently is lower alkyl, or phenyl, $R_2^*$ is lower alkyl, phenyl, alkanoyl having 1 to 6 carbons, or aroyl, and $R_3$ is H, lower alkyl, or phenyl, and W is H, lower alkyl, phenyl, $COOH$, $COOR_4$, $CONHR_4$, $CON(R_4)_2$, where $R_4$ is lower alkyl or a pharmaceutically acceptable salt thereof.

12. A compound of claim 11 where $R_1$ is hydrogen or acyl.

13. A compound of claim 11 where $R_1$ is acetyl.

14. A compound of claim 11 where W is hydrogen.

15. A compound of claim 11 where W is $COOR_4$.

16. A compound of claim 11 where X is long chain alkyl having 5 to 25 carbon atoms.

17. A compound of claim 11 where X is long chain alkyl of 5 to 25 carbons substituted with an aryl group, or long chain alkyl of 5 to 25 carbon substituted with a fluoro substituted aryl group.

18. A compound of claim 11 where Y is $COOH$, $COOR_2$, $CONH_2$, $COR_2$; $COCF_3$, $COCHF_2$, $CH=NOH$, $CR_2=N-OH$, $CH=NOR_2$, $CR_2=NOR_2$, $CH=N-NHR_2$, $CR_2=N-NHR_2$, $C(R_2)_2OH$, $SO_2R_2$, $PO(OR_3)_2$, and $PS(OR_3)_2$.

19. A compound of claim 18 where $R_2$ is methyl or ethyl.

20. A compound of the Formula

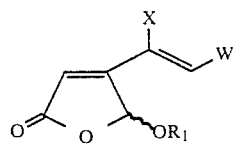

where $R_1$ is H or alkanoyl having 1 to 6 carbons;

X is long chain alkyl having 5 to 25 carbon atoms, long chain alkyl of 5 to 25 carbons substituted with an aryl group, or long chain alkyl of 5 to 25 carbons substituted with a fluoro substituted aryl group;

Y is $COR_2$; $COCF_3$, $COCHF_2$, $PO(OR_3)_2$, and $PS(OR_3)_2$, where $R_2$ independently is lower alkyl, or phenyl, $R_3$ is lower alkyl or a pharmaceutically acceptable salt thereof.

21. A compound of claim 20 where Y is $COCF_3$.

22. A compound of claim 21 where X is $CH_3-(CH_2)_{11}$.

23. The compound of claim 22 where $R_1$ is hydrogen.

24. A compound of claim 20 where Y is $PO(OCH_2CH_3)_2$.

25. A compound of claim 24 where X is $CH_3-(CH_2)_{11}$.

26. The compound of claim 22 where $R_1$ is hydrogen.

27. A compound of the Formula

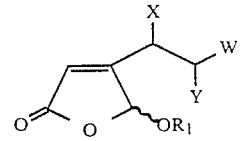

where $R_1$ is H or alkanoyl having 1 to 6 carbons;

X is long chain alkyl having 5 to 25 carbon atoms, long chain alkyl of 5 to 25 carbons substituted with an aryl group, or long chain alkyl of 5 to 25 carbons substituted with a fluoro substituted aryl group;

Y is $COOH$, $COOR_2$, $CONH_2$, $COR_2$, $COCF_3$, $COCHF_2$, $CH=N-NHR_2$, $CH=NOH$, $CR_2=N-OH$, $CH=NOR_2$, $CR_2=NOR_2$, $C(R_2)_2OH$, $SO_2R_2$, $PO(OR_3)_2$, and $PS(OR_3)_2$, where $R_2$ independently is lower alkyl, and $R_3$ independently is lower alkyl, and W is H, lower alkyl or $COOR_4$ where $R_4$ is H or lower alkyl, or a pharmaceutically acceptable salt thereof.

28. A compound of claim 27 where W is hydrogen and X is $CH_3-(CH_2)_{11}$.

29. A compound of claim 28 where Y is $COOCH_2CH_3$.

30. The compound of claim 29 where $R_1$ is hydrogen.

31. A compound of claim 28 where Y is $COCH_3$.

32. The compound of claim 31 where $R_1$ is hydrogen.

33. A compound of claim 28 where Y is $COCF_3$.

34. The compound of claim 33 where $R_1$ is hydrogen.

35. A compound of claim 28 where Y is $C(CH_3)_2OH$.

36. The compound of claim 35 where $R_1$ is hydrogen.

37. A compound of claim 28 where Y is $COOH$.

38. The compound of claim 37 where $R_1$ is hydrogen.

39. A compound of claim 28 where Y is $PO(OCH_2CH_3)_2$.

40. The compound of claim 39 where $R_1$ is hydrogen.

41. A compound of claim 28 where Y is $CONH_2$.

42. The compound of claim 41 where $R_1$ is hydrogen.

43. A compound of claim 28 where Y is $CH=NOH$.

44. The compound of claim 43 where $R_1$ is hydrogen.

45. A compound of claim 28 where Y is $COCF_2H$.

46. The compound of claim 45 where $R_1$ is hydrogen.

47. A compound of claim 28 where Y is $SO_2CH_3$.

48. The compound of claim 47 where $R_1$ is hydrogen.

49. A compound of claim 27 where W is $COOCH_3$ and X is $CH_3-(CH_2)_{11}$.

50. The compound of claim 49 where $R_1$ is hydrogen.

51. A compound of claim 27 where W is hydrogen and X is $(CH_2)_5$-2,4,5-trifluorophenyl.

52. A compound of claim 51 where Y is $COCF_3$.

53. The compound of claim 52 where $R_1$ is hydrogen.

* * * * *

UNITED STATES PATENT AND TRADEMARK OFFICE
CERTIFICATE OF CORRECTION

PATENT NO. : 5,013,850
DATED : May 7, 1991
INVENTOR(S) : Gary C.M. Lee

It is certified that error appears in the above-indentified patent and that said Letters Patent is hereby corrected as shown below:

Column 1, line 23, after "Art", "Manoalide" should start a new paragraph.
Column 1, line 33, after "anti-inflammatory", delete "inflammatory";
Column 2, line 33, "(", second occurrence, should be —)—;
Column 2, line 44, "$CHR_{20}OH$," should be —$CHR_2OH$,—;
Column 2, line 49, "W" should start a new line;
Column 2, line 59, after "pharmaceutically" insert —acceptable—;

UNITED STATES PATENT AND TRADEMARK OFFICE
CERTIFICATE OF CORRECTION

PATENT NO. : 5,013,850
DATED : May 7, 1991
INVENTOR(S) : Gary C.M. Lee

It is certified that error appears in the above-indentified patent and that said Letters Patent is hereby corrected as shown below:

Column 9, line 46, starting with "Alternatively" to line 50 "where $R_1$ is hydrogen." should be deleted.

Column 11, line 68, after "generally" insert —speaking—;

Column 18, line 66, "$(M^+ -2)$" should be —$(M^+ -OH, 2)$—;

Column 19, line 41, before "t," insert —(—;

Column 19, line 43, "1 H" should be —1H—;

Column 20, line 19, "19.6" should be —119.6—;

Column 20, line 44, "$80°-5°/0.5$" should be —$80-5°/0.5$—;

Column 20, line 50, "$(M^-)$" should be —$(M^+)$—;

UNITED STATES PATENT AND TRADEMARK OFFICE
CERTIFICATE OF CORRECTION

PATENT NO. : 5,013,850
DATED : May 7, 1991
INVENTOR(S) : Gary C.M. Lee

It is certified that error appears in the above-indentified patent and that said Letters Patent is hereby corrected as shown below:

Column 21, line 19, "40°-5°" should be —40-5°—;
Column 21, line 41, "12 H" should be —12H—;
Column 21, line 42, "20 H" should be —20H—;
Column 21, line 46, "29.3" should be —29.3—;
Column 22, line 44, before "s" (second occurrence) insert —(—;
Column 22, line 49, "(M+NH$_4$)$^-$" should be —(M+NH$_4$)$^+$—;
Column 23, line 34, "86" should be —5.86—;
Column 24, line 6, after "4" there should be no space.
Column 27, line 3, before "m," insert —(—;
Column 27, line 3, "(t, 6H), J = 7.1 Hz)," should be —(t, 6H, J = 7.1 Hz),—;
Column 28, line 6, "161.0" should be —162.0—;
Column 28, line 65, "85°-90°/0.4" should be —85-90°/0.4—;
Column 30, line 48 (Claim 9), "CR$_2$=NHR$_2$," should be —CR$_2$=N-NHR$_2$,—; and
Column 31, lines 35-42 (Claim 20), the "W" in the formula should be —Y—.

Signed and Sealed this

Fourteenth Day of September, 1993

Attest:

BRUCE LEHMAN

*Attesting Officer*　　　*Commissioner of Patents and Trademarks*

UNITED STATES PATENT AND TRADEMARK OFFICE
CERTIFICATE OF CORRECTION

PATENT NO. : 5,013,850
DATED : May 7, 1991
INVENTOR(S) : Gary C. M. Lee It is certified that error appears in the above-identified patent and that said Letters Patent is hereby corrected as shown below:

Column 24, line 59, "wa" should be --was--; and

Column 29, line 31, "rection" should be --reaction--.

Signed and Sealed this

Nineteenth Day of October, 1993

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,013,850
DATED : May 7, 1991
INVENTOR(S) : Gary C.M. Lee

It is certified that error appears in the above-indentified patent and that said Letters Patent is hereby corrected as shown below:

Column 4, in Reaction Scheme 1, Formulas 1-4, "Sl" should be --Si--;

Columns 4-5, in Reaction Scheme 2, Formulas 8 and 3, "Sl" should be --Si--;

Columns 5-6, Reaction Scheme 3, formulas 3, 13, and 14, "Sl" should be --Si--

Columns 7-8, Reaction Scheme 4, Formulas 3, 15, 17, 18, and 19, "Sl" should be --Si--;

Column 8, Reaction Scheme 5, Formula 20, "Sl" should be --Cl--;

Columns 9-10, Reaction Scheme 5, Formula 21, "Cl" should be --Si--;

Columns 9-10, Reaction Scheme 5, Formula 22, "Sl" should be --Si--;

Signed and Sealed this

Twenty-ninth Day of November, 1994

Attest:

BRUCE LEHMAN

*Attesting Officer*     *Commissioner of Patents and Trademarks*